US010022205B2

(12) United States Patent
Tsuji et al.

(10) Patent No.: US 10,022,205 B2
(45) Date of Patent: Jul. 17, 2018

(54) DENTAL IMPLANT AND METHOD FOR PRODUCING SAME

(71) Applicant: Organ Technologies, Inc., Tokyo (JP)

(72) Inventors: Takashi Tsuji, Tokyo (JP); Masamitsu Oshima, Tokyo (JP)

(73) Assignee: ORGAN TECHNOLOGIES, INC., Tokyo (JP)

( * ) Notice: Subject to any disclaimer, the term of this patent is extended or adjusted under 35 U.S.C. 154(b) by 44 days.

(21) Appl. No.: 14/375,715

(22) PCT Filed: Jan. 28, 2013

(86) PCT No.: PCT/JP2013/051746
§ 371 (c)(1),
(2) Date: Jul. 30, 2014

(87) PCT Pub. No.: WO2013/115128
PCT Pub. Date: Aug. 8, 2013

(65) Prior Publication Data
US 2014/0356797 A1 Dec. 4, 2014

(30) Foreign Application Priority Data

Feb. 1, 2012 (JP) .................................. 2012-020359
Feb. 2, 2012 (JP) .................................. 2012-020697

(51) Int. Cl.
*A61C 8/00* (2006.01)
*A61L 27/32* (2006.01)
(Continued)

(52) U.S. Cl.
CPC .............. *A61C 8/0013* (2013.01); *A61D 5/00* (2013.01); *A61K 6/0038* (2013.01);
(Continued)

(58) Field of Classification Search
CPC .... A61C 8/0006; A61C 8/0012; A61C 8/0013
(Continued)

(56) References Cited

U.S. PATENT DOCUMENTS 4,725,234 A * 2/1988 Ethridge ................. A61C 17/00
433/215
5,533,836 A * 7/1996 Moore ............... A61K 38/1858
435/384

(Continued)

FOREIGN PATENT DOCUMENTS

DE 102009057502 A1 3/2015
JP 6-7381 A 1/1994

(Continued)

OTHER PUBLICATIONS

Choi Byung-Ho, "Periodontal Ligament Formation Around Titanium Implants Using Cultured Periodontal Ligament Cells: A Pilot Study", *The International Journal of Oral and Maxillofacial Implants*, 2000, vol. 15, No. 2, pp. 193-196.

(Continued)

*Primary Examiner* — Nicholas Lucchesi
(74) *Attorney, Agent, or Firm* — Myers Bigel, P.A.

(57) ABSTRACT

The object of the present invention is to provide an implant that enables functional periodontium formation around the implant after transplantation of a dental implant. In some aspects of the present invention, a tooth germ tissue-derived or a periodontal membrane tissue-derived cell mass is placed on the surface of the implant, and the surface of the implant on which the cell mass is placed is the whole or a part of the surface which is surrounded by the alveolar bone of the recipient at the time of implant transplantation.

16 Claims, 20 Drawing Sheets

(51) Int. Cl.
*A61L 27/34* (2006.01)
*A61L 27/36* (2006.01)
*A61L 27/38* (2006.01)
*A61K 6/00* (2006.01)
*A61D 5/00* (2006.01)
*A61K 6/033* (2006.01)

(52) U.S. Cl.
CPC .......... *A61K 6/0044* (2013.01); *A61K 6/0085* (2013.01); *A61K 6/033* (2013.01); *A61L 27/32* (2013.01); *A61L 27/34* (2013.01); *A61L 27/365* (2013.01); *A61L 27/3608* (2013.01); *A61L 27/3821* (2013.01); *A61L 27/3834* (2013.01); *A61L 27/3865* (2013.01); *A61L 2430/12* (2013.01)

(58) Field of Classification Search
USPC .......................................... 433/201.1, 202.1
See application file for complete search history.

(56) References Cited

U.S. PATENT DOCUMENTS

| | | | | |
|---|---|---|---|---|
| 5,604,204 A * | 2/1997 | Ammann | ................... | A61F 2/28 424/422 |
| 6,132,214 A * | 10/2000 | Suhonen | ................... | A61C 8/00 433/201.1 |
| 6,409,764 B1 * | 6/2002 | White | ................... | A61C 8/0006 424/424 |
| 7,497,686 B2 * | 3/2009 | Sharpe | ................. | A61L 27/3604 433/215 |
| 8,071,083 B2 * | 12/2011 | De Bruijn | ................ | A61L 27/12 424/422 |
| 8,114,841 B2 * | 2/2012 | Lynch | ..................... | A61L 27/12 424/484 |
| 8,602,780 B2 * | 12/2013 | Rubbert | ................. | A61C 5/007 433/173 |
| 8,870,954 B2 * | 10/2014 | Lynch | ..................... | A61L 27/24 424/426 |
| 2001/0055745 A1 * | 12/2001 | Gault | ..................... | A61C 8/0012 433/201.1 |
| 2003/0026770 A1 * | 2/2003 | Szymaitis | ................ | A61L 27/24 424/50 |
| 2003/0175656 A1 * | 9/2003 | Livne | ................. | A61B 17/6441 433/201.1 |
| 2004/0053968 A1 * | 3/2004 | Hartman | ............... | A61K 31/365 514/333 |
| 2005/0171015 A1 * | 8/2005 | Crabtree | ............ | A61K 38/1709 514/9.4 |
| 2006/0024249 A1 * | 2/2006 | Yelick | ................. | A61L 27/3804 424/50 |
| 2006/0039896 A1 * | 2/2006 | Kleinsek | ............. | A61L 27/3633 424/93.7 |
| 2007/0005138 A9 * | 1/2007 | Goulet | ...................... | A61F 2/08 623/13.17 |
| 2007/0111164 A1 * | 5/2007 | Saade | .................. | A61C 8/0022 433/174 |
| 2007/0254005 A1 * | 11/2007 | Pathak | ................... | A61K 35/12 424/423 |
| 2008/0095815 A1 * | 4/2008 | Mao | ..................... | A61C 8/0012 424/422 |
| 2009/0016996 A2 * | 1/2009 | Kleinsek | ............. | A61K 38/1808 424/93.7 |
| 2009/0130631 A1 * | 5/2009 | Chen | .................... | A61C 8/0022 433/174 |
| 2010/0172863 A1 * | 7/2010 | Wasielewski | ........ | A61K 9/0009 424/85.2 |
| 2011/0306135 A1 * | 12/2011 | Tsuji | ................... | A61L 27/3865 435/395 |
| 2012/0141562 A1 * | 6/2012 | Achneck | ................ | A61L 27/28 424/400 |
| 2012/0282573 A1 * | 11/2012 | Mao | ........................ | A61L 27/46 433/202.1 |
| 2013/0089827 A1 * | 4/2013 | Tsuji | ...................... | A61L 27/24 433/1 |
| 2013/0309208 A1 * | 11/2013 | Wasielewski | ...... | A61K 38/1709 424/93.7 |

FOREIGN PATENT DOCUMENTS

| | | |
|---|---|---|
| JP | 2003-144139 A | 5/2003 |
| JP | 2006-76980 A | 3/2006 |
| WO | WO2006/010600 A2 | 2/2006 |
| WO | WO 2009/151614 A2 | 12/2009 |

OTHER PUBLICATIONS

Craig RG et al., "Effects of Periodontal Cell Grafts and Enamel Matrix Proteins on the Implant-Connective Tissue Interface: A Pilot Study in the Minipig", *Journal of Oral Implantology* 2006; 32(5): 228-36.

Lin Y. et. al., "Bioengineered Periodontal Tissue Formed on Titanium Dental Implants", *Journal of Dental Research*. 2011; 90(2): 251-6. Originally published online Dec. 13, 2010.

Gault Phillippe et al., *Tissue-engineered ligament: implant constructs for tooth replacement*, Journal of Clinical Periodontology, 2010, vol. 37, Issue 8, pp. 750-758.

International Search Report and Written Opinion Corresponding to International Application No. PCT/JP2013/051746; dated Apr. 9, 2013.

European Search Report, corresponding to European Patent Application EP13743314, dated Aug. 20, 2015, 6 pages.

Veterinary Periodontal Disease, 2002, 6 pages.

* cited by examiner

[Figure 1]
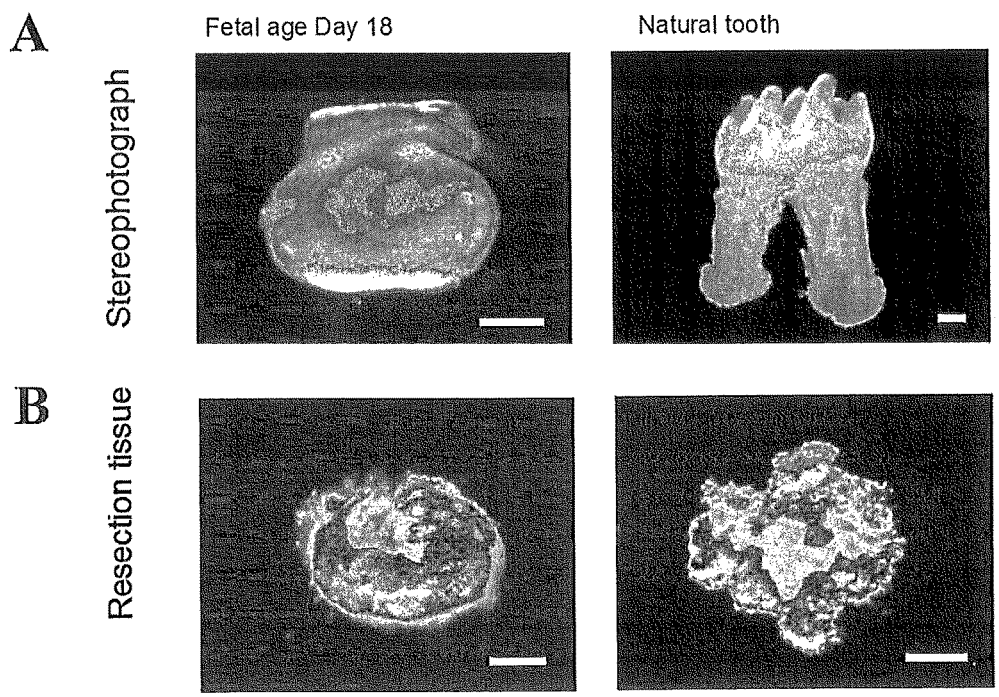

[Figure 2]
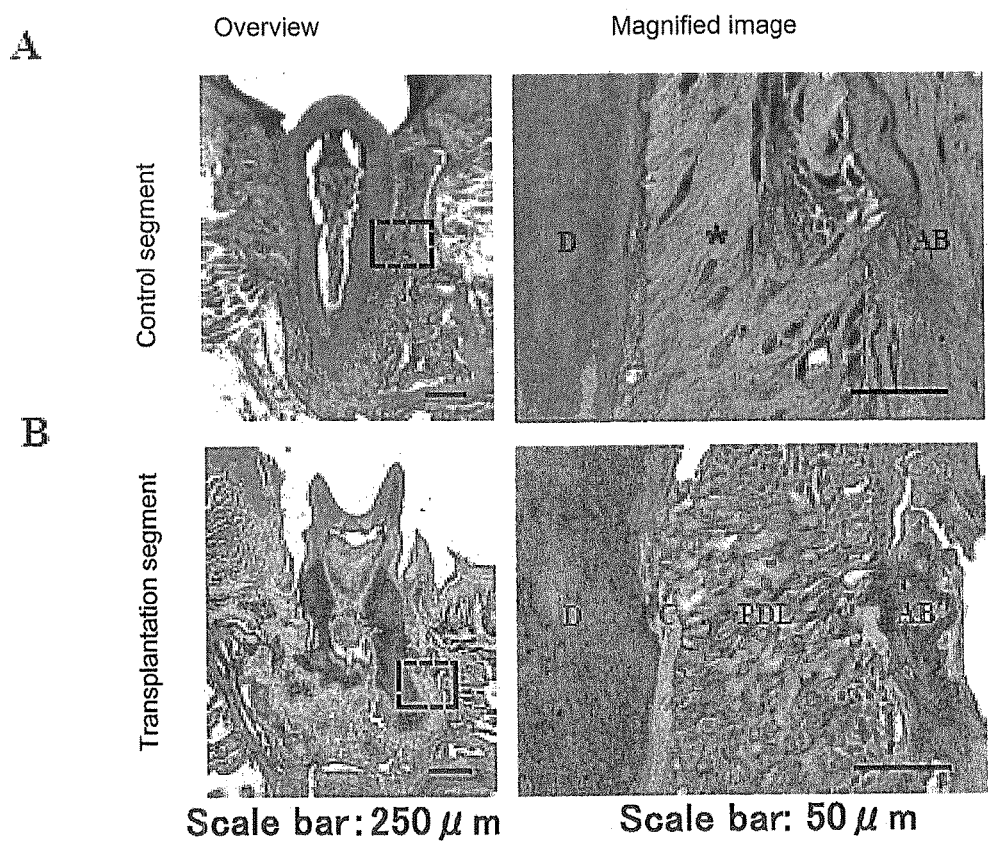

[Figure 3]
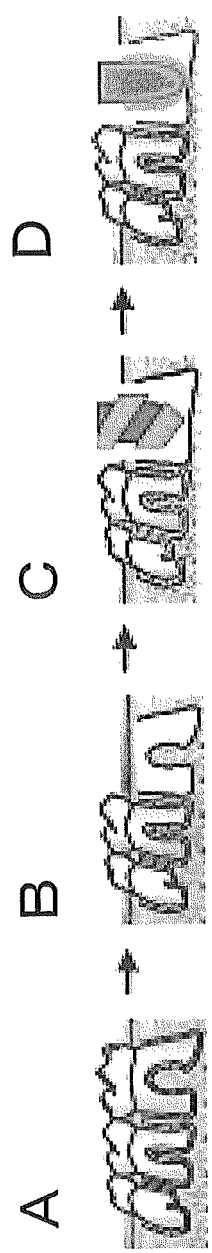

[Figure 4]
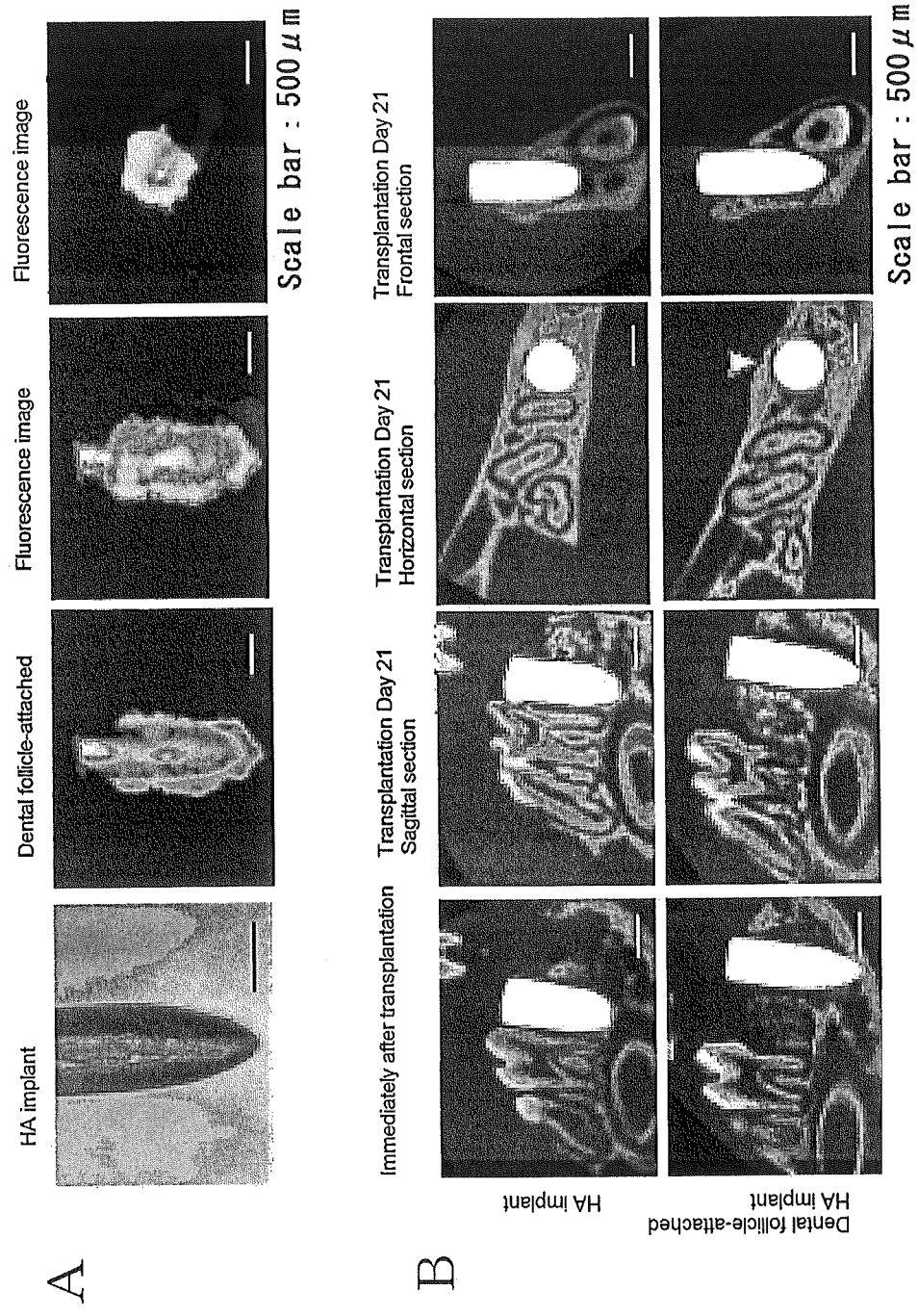

[Figure 5]
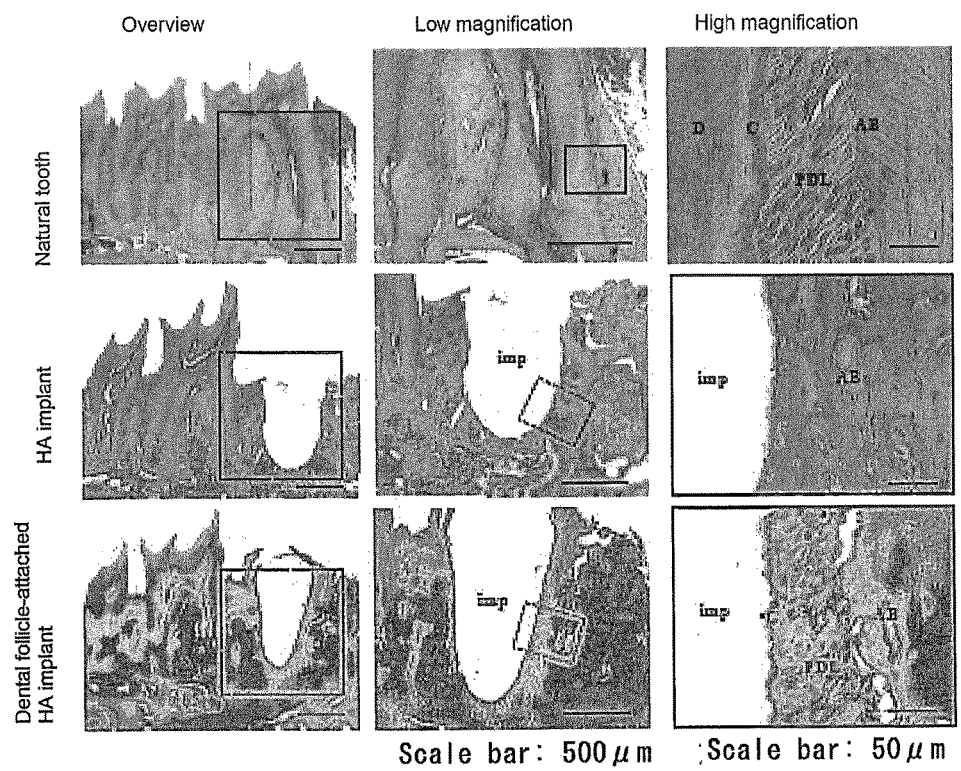

[Figure 6]
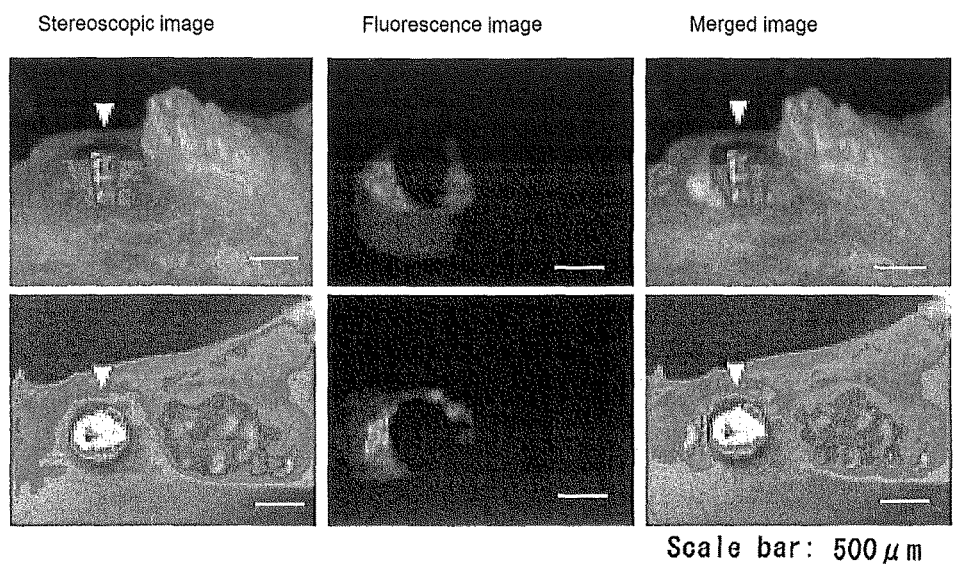
[Figure 7]
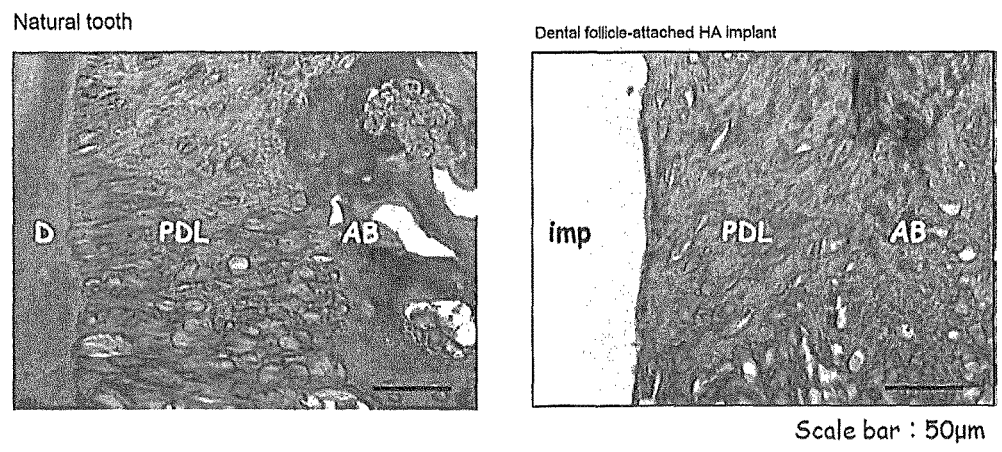

[Figure 8]
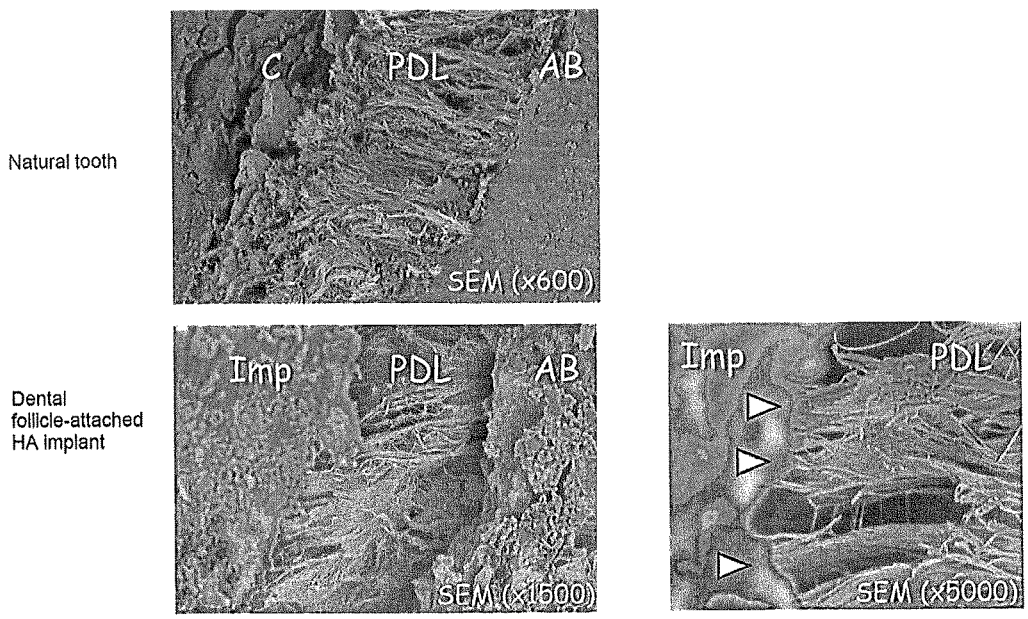
Natural tooth
Dental follicle-attached HA implant

[Figure 9]
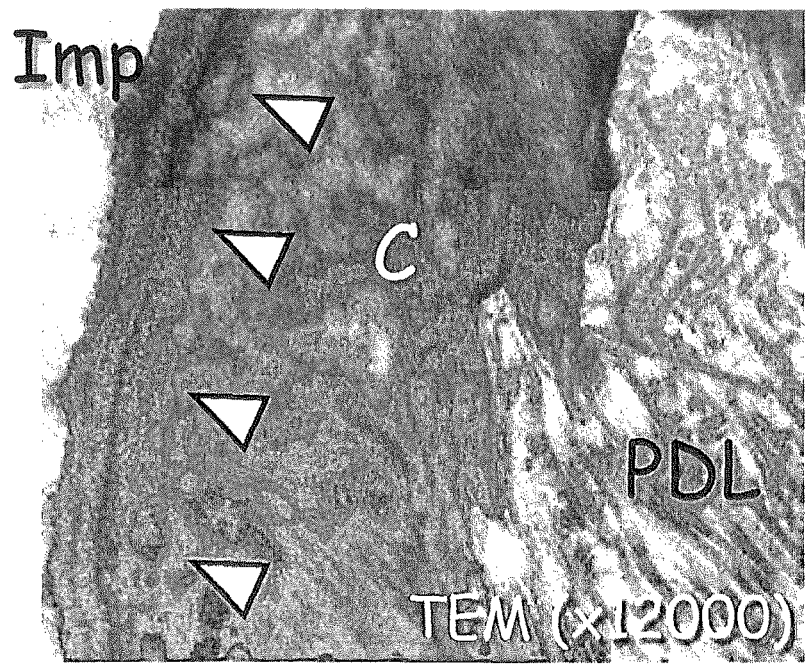
[Figure 10]
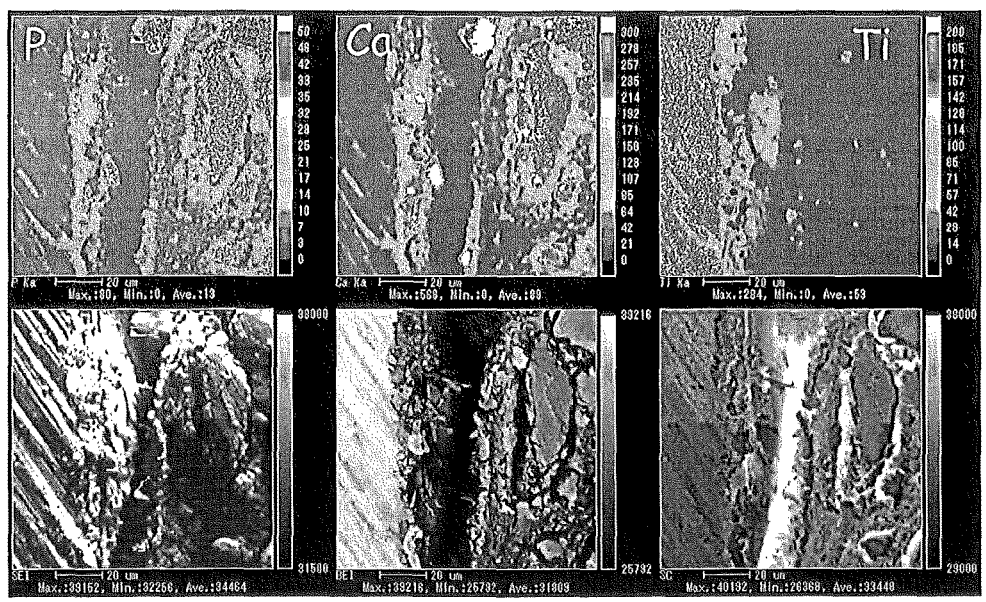

[Figure 11]
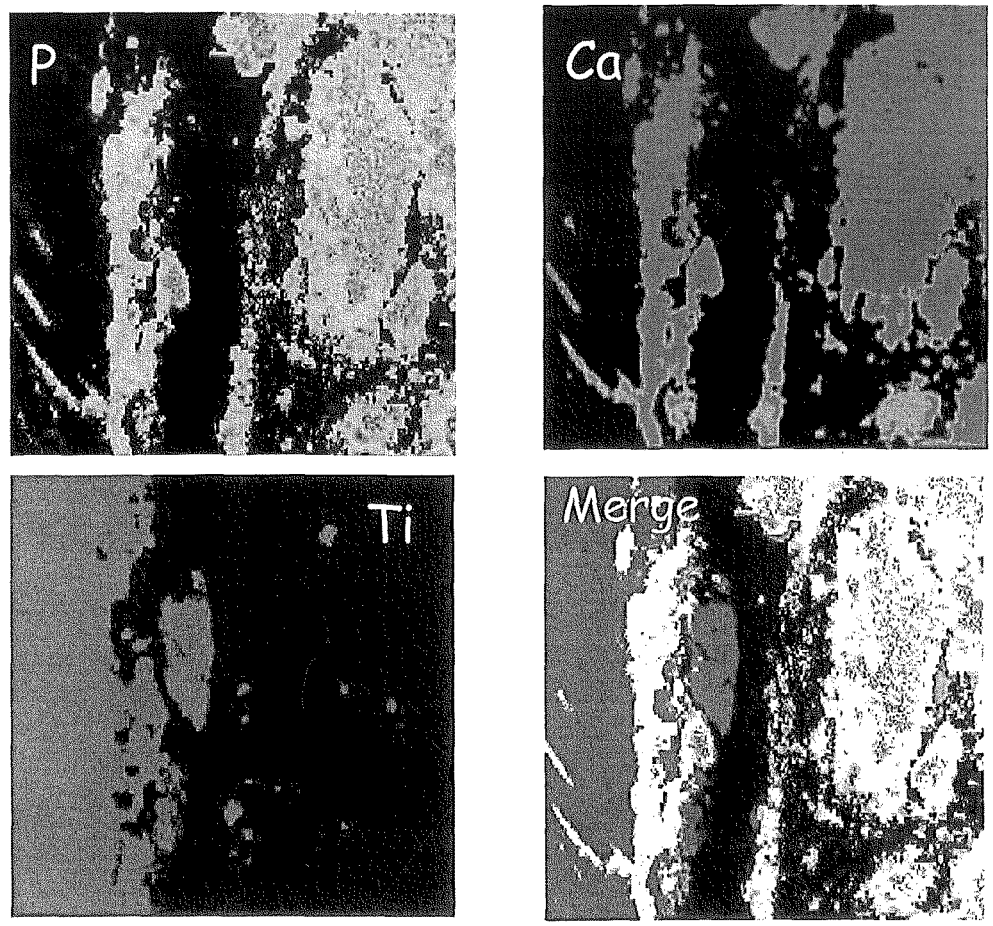

[Figure 12]
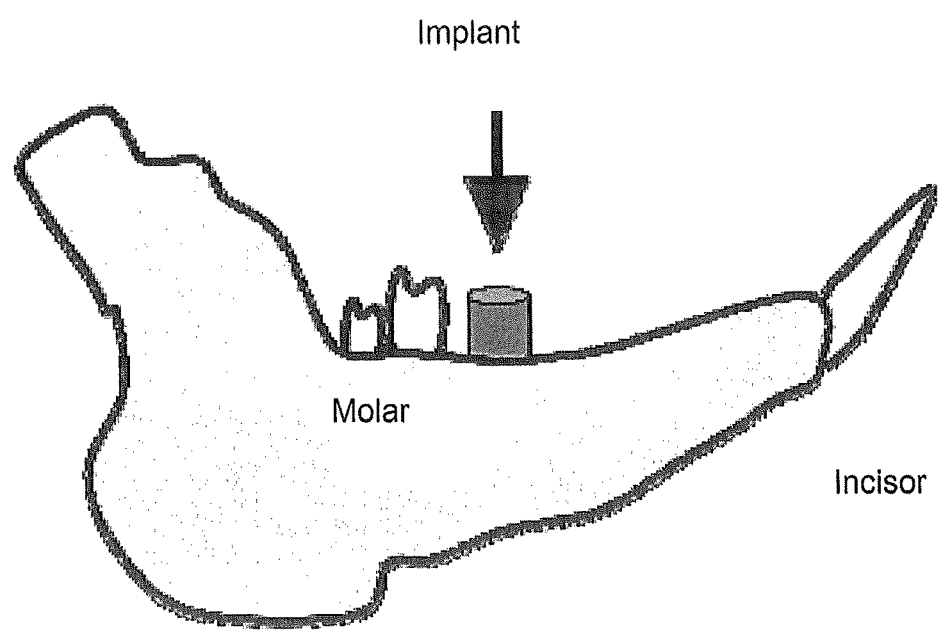

[Figure 13]
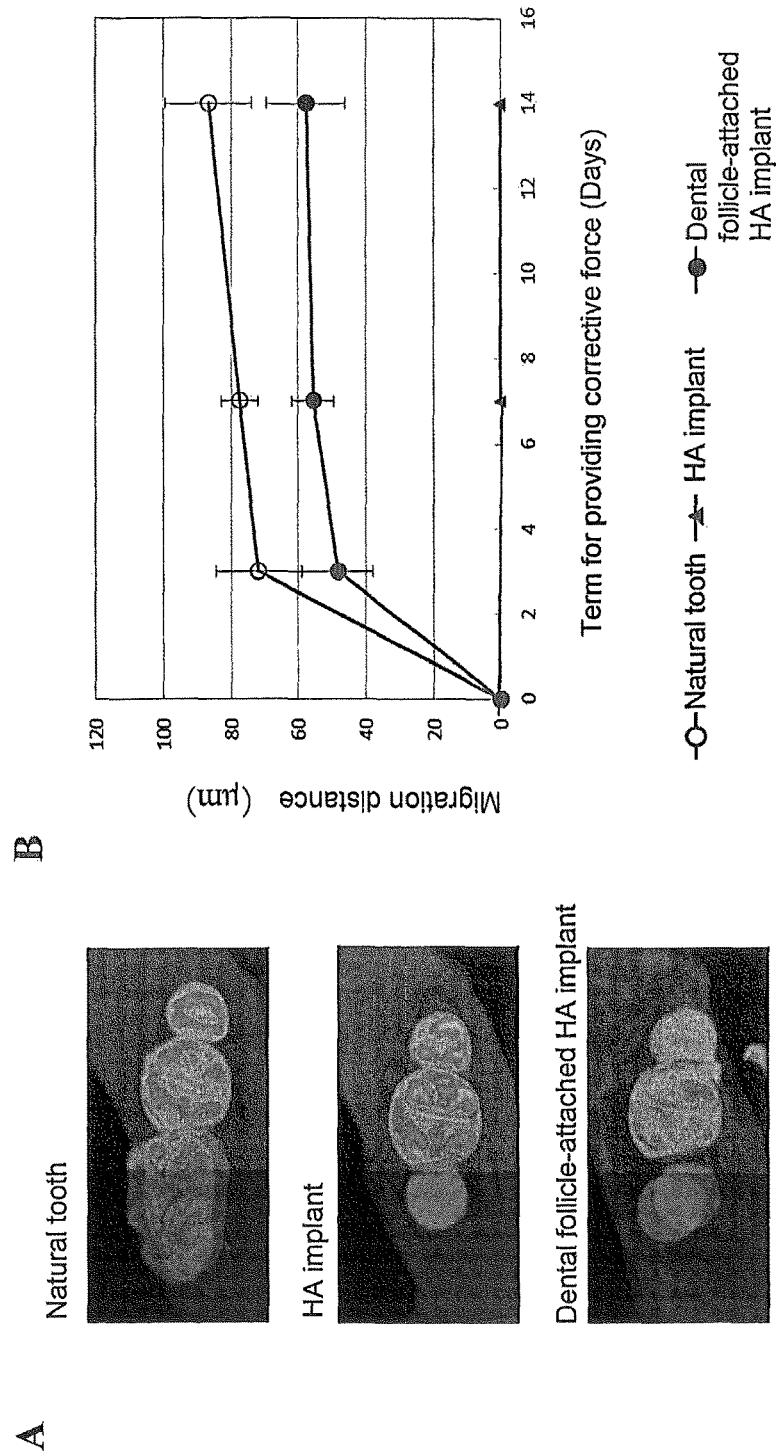

[Figure 14]
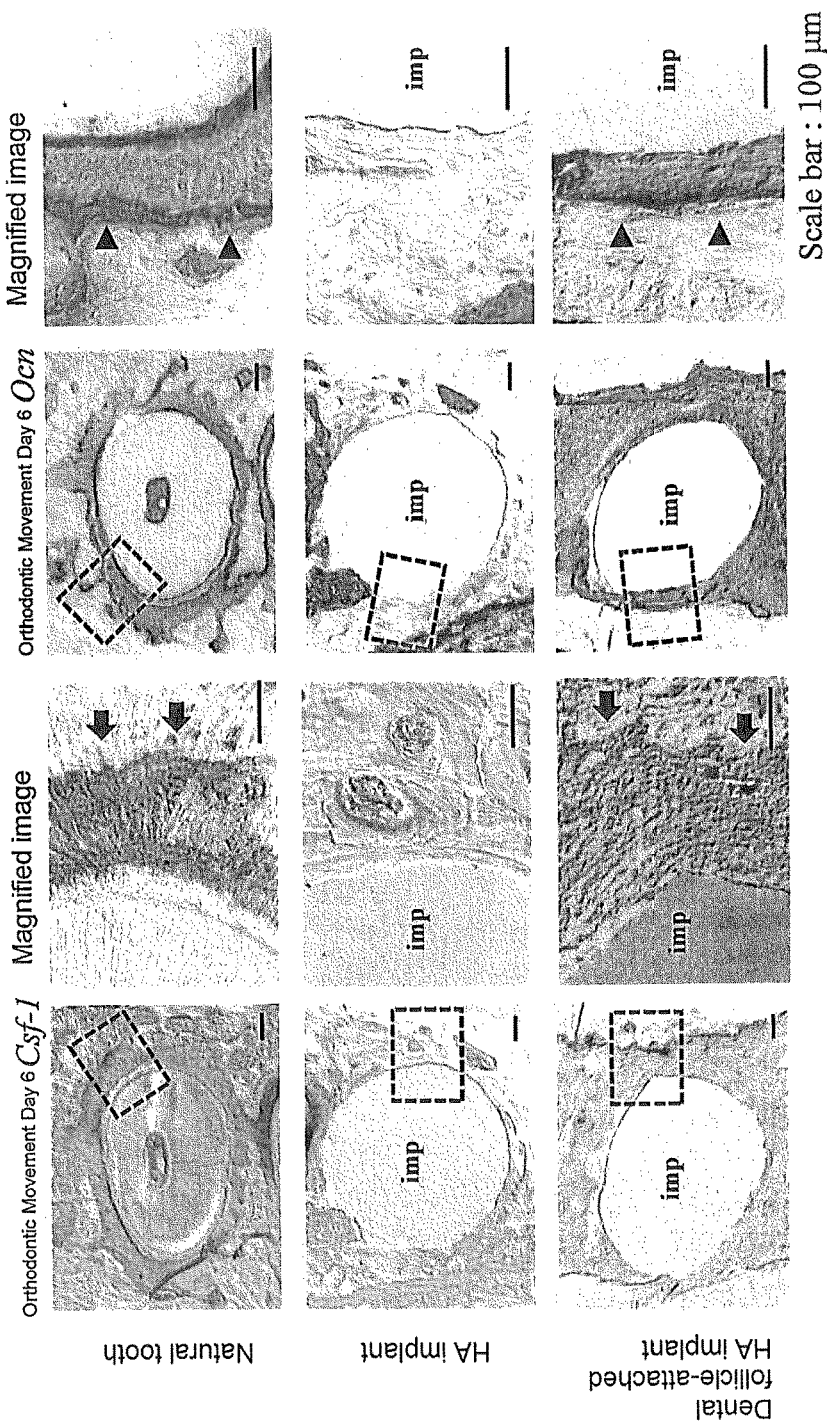

[Figure 15]
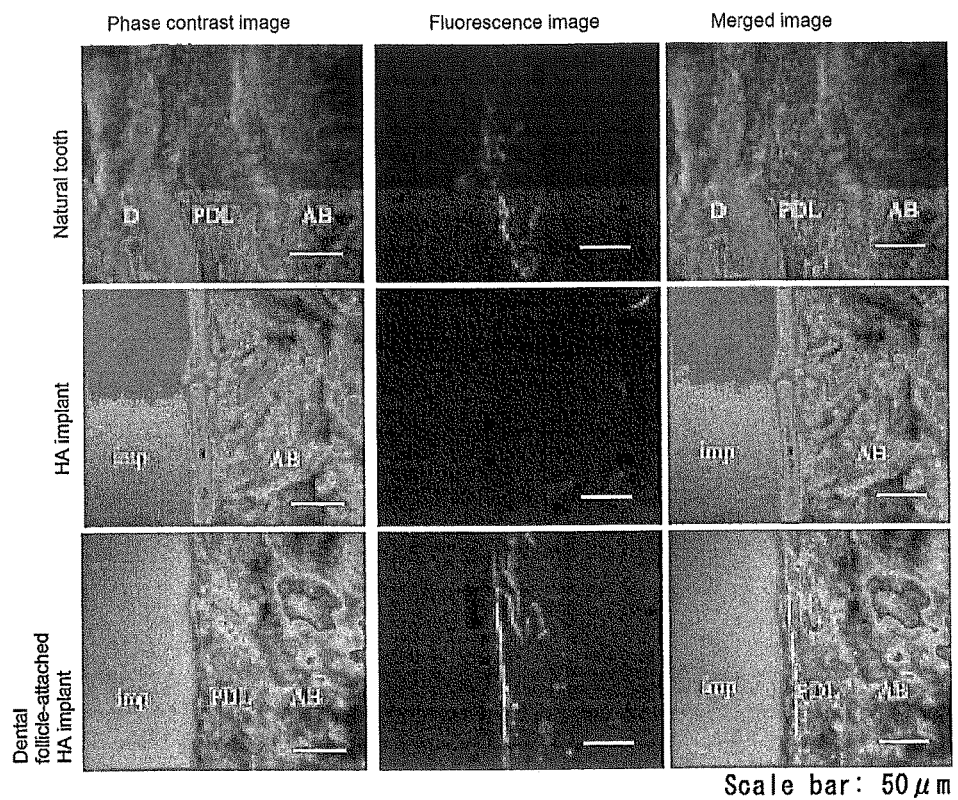

[Figure 16]
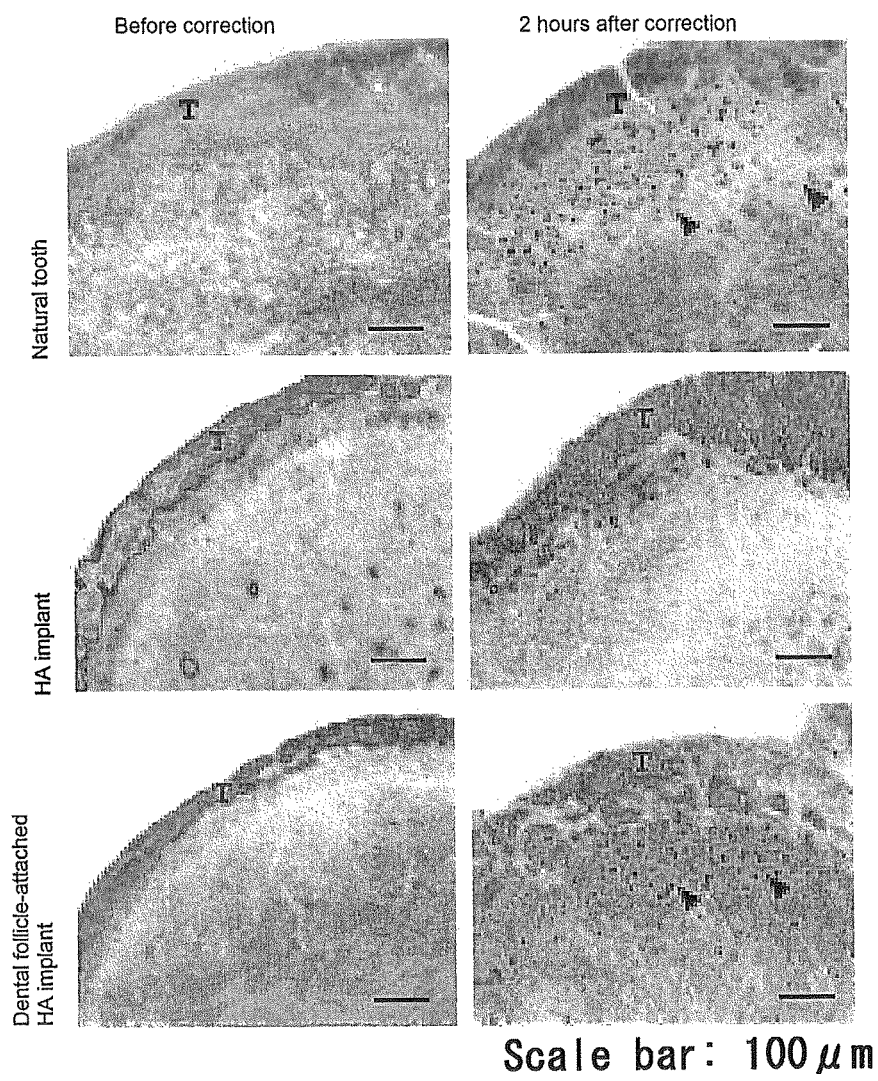

[Figure 17]
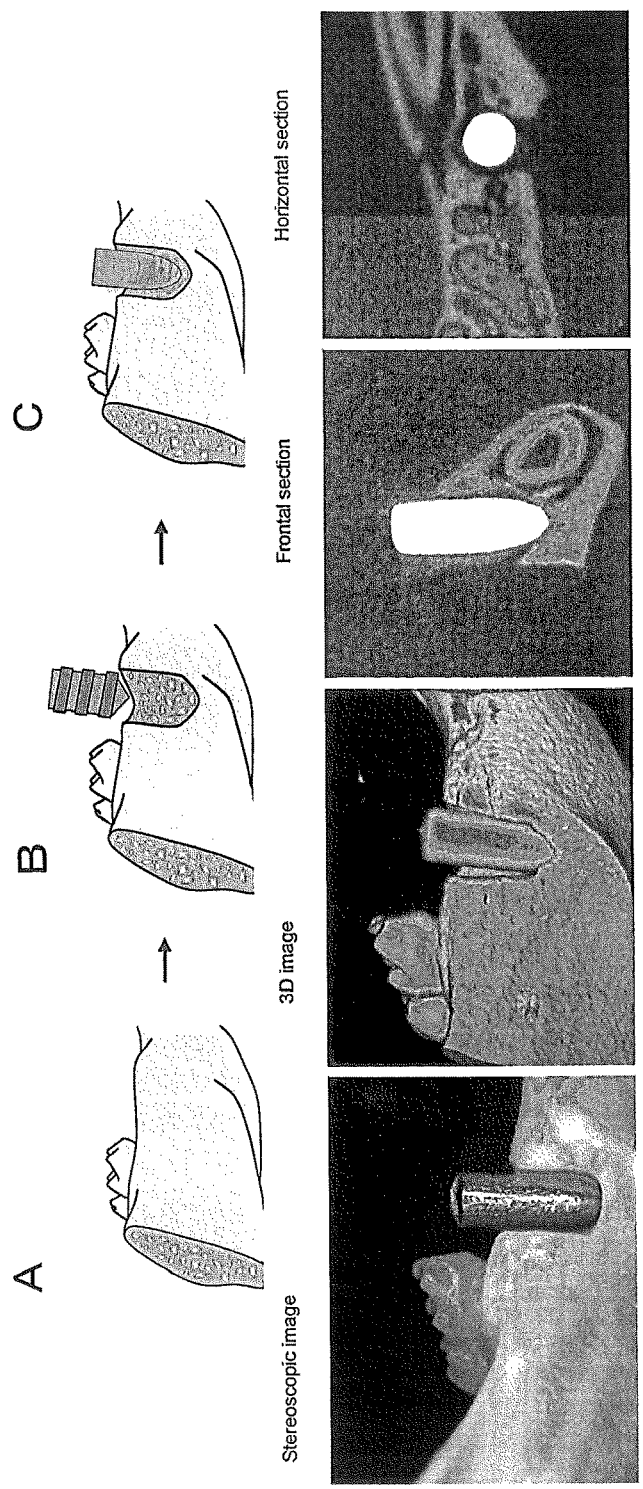

[Figure 18]
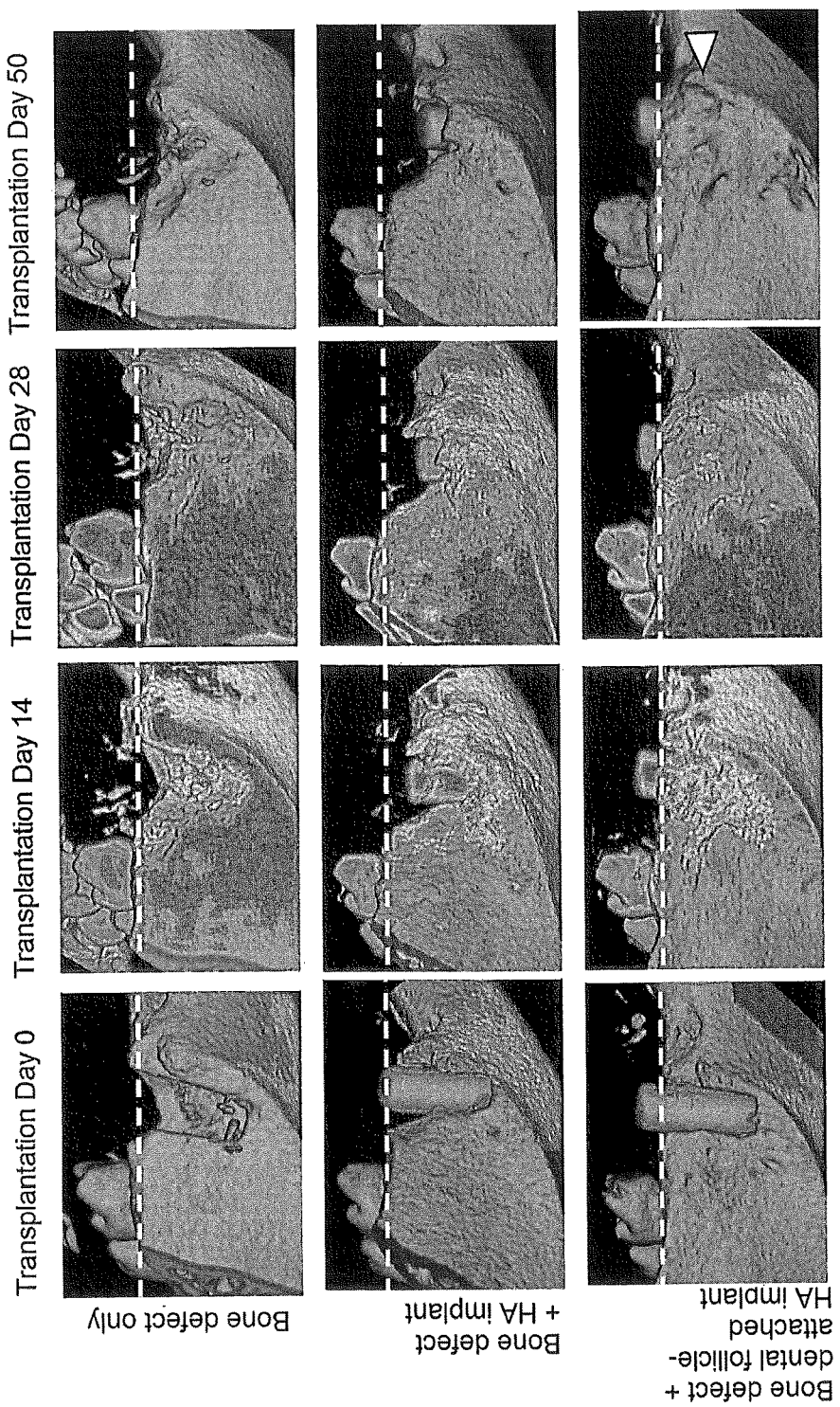

[Figure 19]
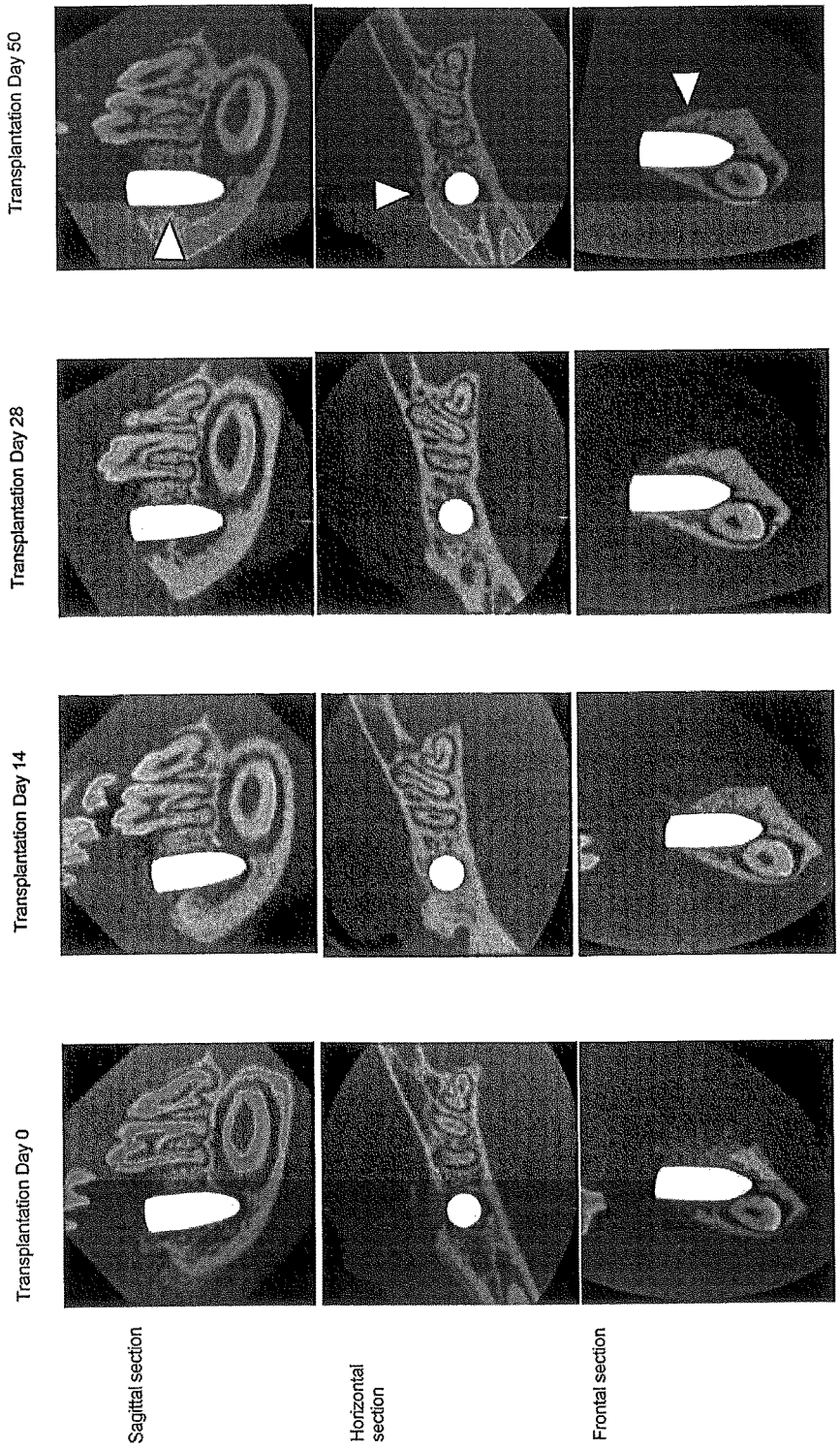

[Figure 20]
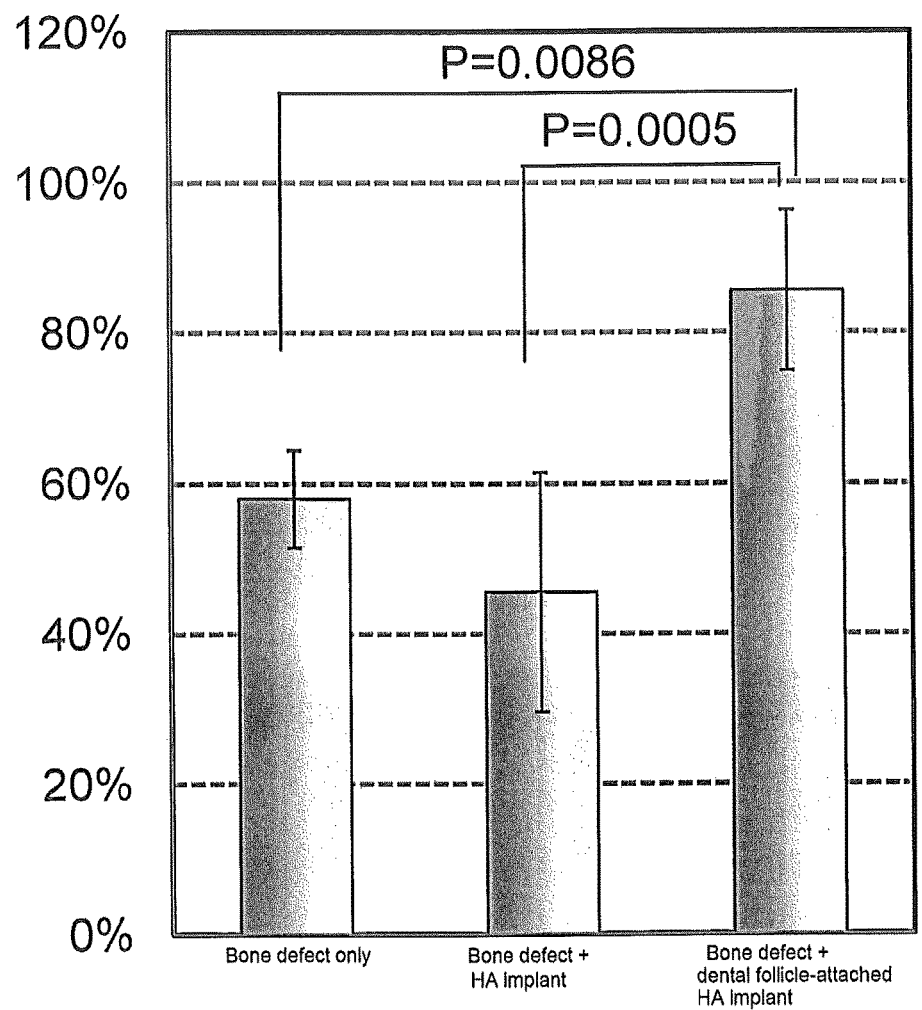

[Figure 21]
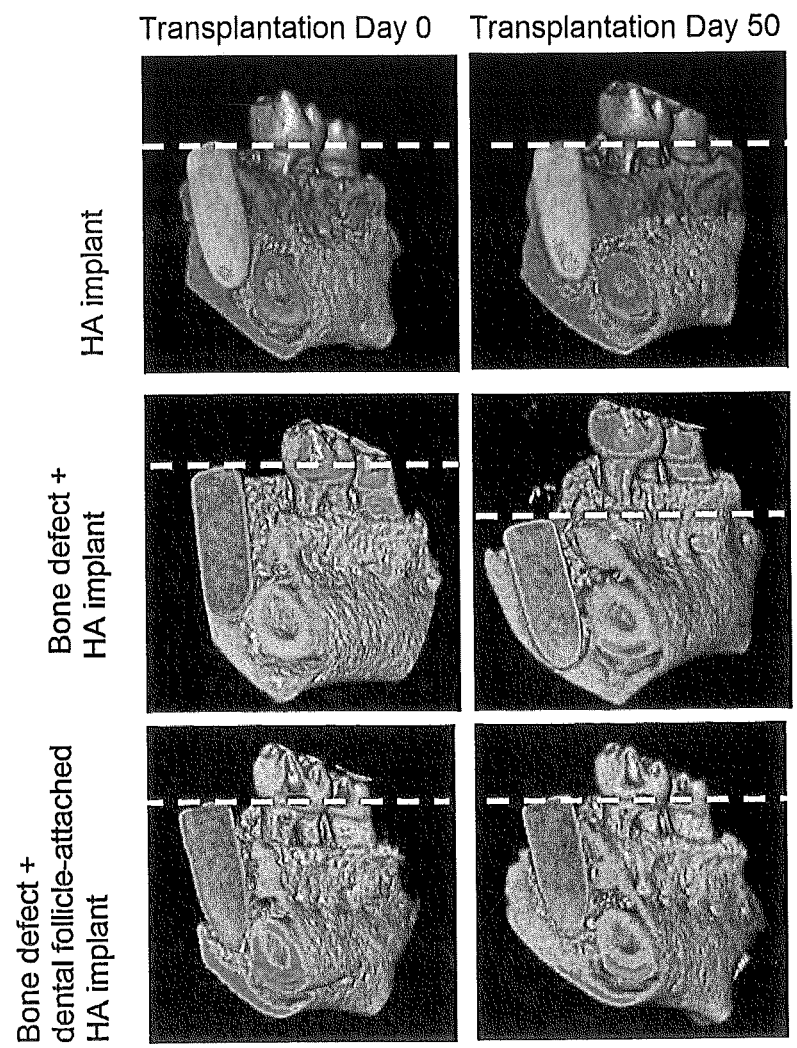

[Figure 22]
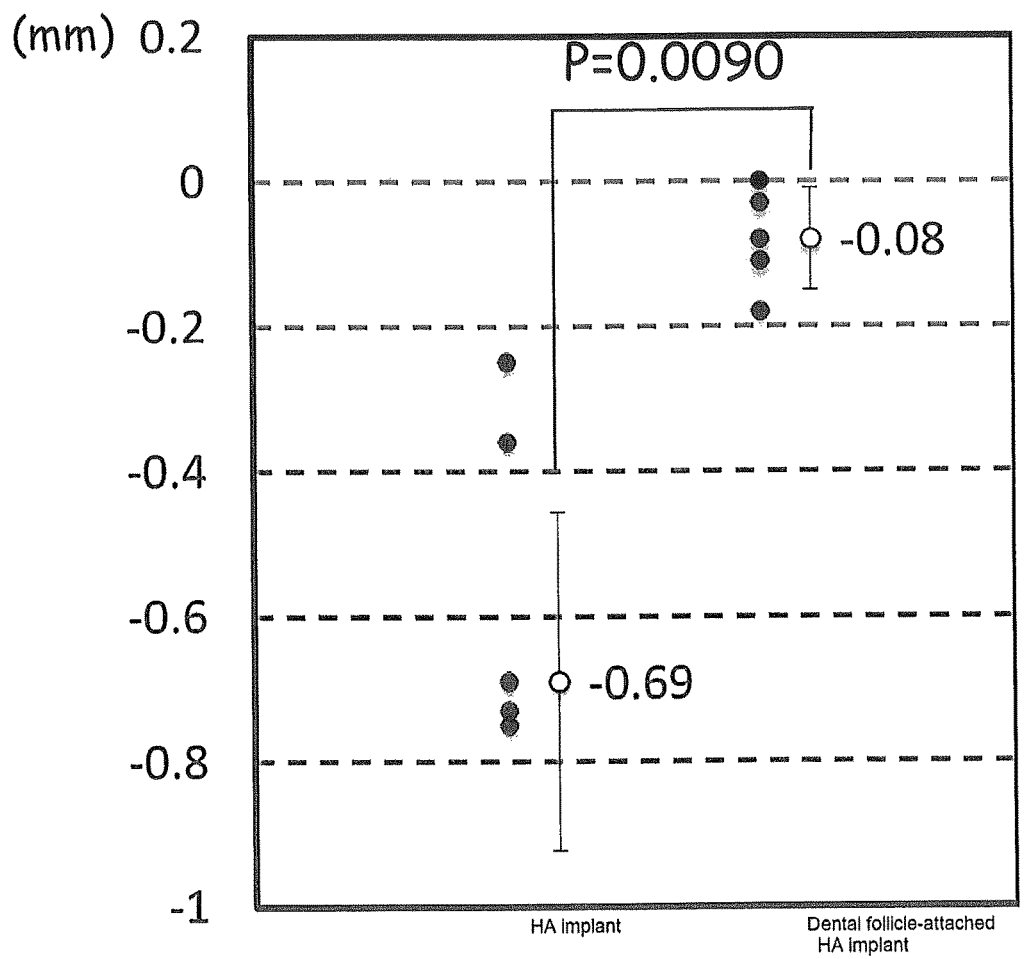

DENTAL IMPLANT AND METHOD FOR PRODUCING SAME

STATEMENT OF PRIORITY

This application is a 35 U.S.C. § 371 national phase application of International Application Serial No. PCT/JP2013/051746, filed Jan. 28, 2013, which claims the benefit, under 35 U.S.C. § 119 (a) of Japanese Patent Application No. 2012-020697, filed Feb. 2, 2012, and Japanese Patent Application No. 2012-020359, filed Feb. 1, 2012, the entire contents of each of which are incorporated by reference herein.

TECHNICAL FIELD

The present invention relates to a dental implant and a manufacturing method thereof. More specifically, the present invention relates to a dental implant that enables functional periodontium formation and a manufacturing method thereof.

BACKGROUND ART

Various therapeutic means are known for regaining tooth function which was lost by dental caries or periodontal disease. For example, a method for embedding an artificial tooth prepared from artificial materials such as metals or ceramics into the tooth root is known. Moreover, for example, if the loss is completely to the tooth root, a method for placing an artificial tooth while constructing a bridge between healthy teeth is known.

Further, oral cavity implant therapy has been conducted in recent years as one advanced therapeutic method of this dental substitution medical care. Oral cavity implant therapy is a means for setting an artificial tooth root such as titanium in the jaw bone of the site of lost tooth.

However, there is a significant difference between the tooth root of a natural tooth and a dental implant (artificial tooth root), in that the tooth root of a natural tooth is covered with periodontal membrane which is a part of the periodontium, whereas a dental implant transplantation site ordinarily does not have periodontal membrane.

Around at the natural tooth, there exist fibrous periodontal membrane tissue that connects the cementum on the tooth root side and the exterior alveolar bone. The cementum has the functions of protecting the tooth root surface and attaching the periodontal membrane to the tooth root surface. In addition, the periodontal membrane is known to have three functions broadly divided into: 1) an occlusal force cushioning effect, 2) a tooth migration ability (mechanics employed for orthodontic therapy and the like), and 3) a neurotransmission function of transmitting noxious stimulation (such as pain stimulation) such as occlusion and correction to the central nervous system. Among these, the periodontal membrane in particular has fibers running vertically to the longitudinal direction of the tooth root in order to cushion the occlusal force of teeth, and this running of the fiber in the periodontal membrane tissue is known to be an essential configuration for the functional expression of the periodontal membrane.

However, when a dental implant is transplanted, functional periodontium like those existing around the natural tooth cannot be formed at the implant transplantation site. For this reason, there was a problem with the dental implant transplantation site that absorption of the alveolar bone supporting the implant is caused by the occlusal force in long-term use, and it would no longer be able to withstand to use.

Accordingly, a technology that also enables the formation of periodontium similar to that of a natural tooth when a dental implant is transplanted has been long desired.

Until now, employment of periodontal tissue-derived cultured cells in order to allow formation of periodontium around the implant after transplantation has been investigated.

<Non-Patent Literature 1>

This literature discloses the utilization of progenitor cell-derived cultured cells collected from rat periodontal membrane. The literature discloses coating the implant treated with SLA with the cultured cells and Matrigel. The literature also mentions that periodontium was formed when this implant was transplanted to the tooth loss site of a rat.

However, the running of the periodontal membrane formed around the implant in the literature is parallel to the longitudinal direction of the implant, and differs from natural periodontal membrane. Since the running of periodontal membrane has an important meaning in supporting the occlusal force of teeth, a function to support occlusal force could not be expected with periodontium having such periodontal membrane.

<Non-Patent Literature 2>

This literature discloses a method of transplanting a titanium implant treated with EMD (Emdogain) to the jaw bone, and at the same time injecting PDL cells collected from the periodontal membrane into the transplantation site. This method uses a combination of agents with enamel matrix protein as the main component in order to attempt formation of periodontium around the implant. The literature also mentions the formation of tissue bound to the alveolar bone without epithelium tissue. However, the structure of the cementum which is one of periodontium is not observed in the periodontium formed. In addition, the running of a periodontal membrane in the periodontium is also not verified.

As such, a dental implant that enables the formation of functional periodontium has not yet been reported.

CITATION LIST

[Non-Patent Literature 1] Lin Y et. al., J Dent Res. 2011 Feb.; 90 (2): 251-6. Epub 2010 Dec. 13.
[Non-Patent Literature 2] Craig R G et al., J Oral Implantol. 2006; 32 (5): 228-36.

SUMMARY OF THE INVENTION

Problems to be Solved by the Invention

The object of the present invention is to provide an implant that enables functional periodontium formation around the implant after transplantation of a dental implant.

Means for Solving the Problems

As a result of extensive investigation by the present inventors in order to solve the above problem, we found that by placing a tooth germ tissue-derived or a periodontal membrane tissue-derived cell mass on the surface of the dental implant, functional periodontium can be formed around the implant after implant transplantation.

In other words, the present invention relates to a dental implant that enables functional periodontium formation, characterized in that a tooth germ tissue-derived or a periodontal membrane tissue-derived cell mass is placed on the surface of said implant, and the surface of said implant on which said cell mass is to be placed is the whole or a part of the surface which is surrounded by the alveolar bone of the recipient at the time of transplantation of said implant.

Here, one embodiment of the dental implant of the present invention that enables functional periodontium formation is characterized in that said tooth germ tissue-derived cell mass is a tooth germ mesenchymal tissue-derived or a dental follicle tissue-derived cell mass.

One embodiment of the dental implant of the present invention that enables functional periodontium formation is also characterized in that said cell mass is derived from tooth germ tissue, and said tooth germ tissue is in any one developmental stage selected from the group consisting of the cap stage, the early bell stage, and the late bell stage.

One embodiment of the dental implant of the present invention that enables functional periodontium formation is also characterized in that said implant is correctable after implant transplantation.

One embodiment of the dental implant of the present invention that enables functional periodontium formation is also characterized in that said periodontium formed has at least one characteristic among (i) having functional cementum and functional periodontal membrane, and (ii) having functional nerve fiber.

One embodiment of the dental implant of the present invention that enables functional periodontium formation is also characterized in that said implant further comprises a coating layer of a surface coating agent on the entire surface of the implant or a part thereof, and said cell mass is placed on the surface of said coating layer.

One embodiment of the dental implant of the present invention that enables functional periodontium formation is also characterized in that said surface coating agent is selected from the group consisting of hydroxyapatite, α-tricalcium phosphate, β-tricalcium phosphate, and collagen.

One embodiment of the dental implant of the present invention that enables functional periodontium formation is also characterized in that said implant can promote the regeneration of the alveolar bone.

One embodiment of the dental implant of the present invention that enables functional periodontium formation is also characterized in that said implant can improve the regenerative capacity of the alveolar bone.

Needless to say, any combination of one or more characteristics of the present invention described above is also a dental implant of the present invention.

Moreover, another aspect of the present invention relates to a method for manufacturing a dental implant that enables the formation of functional periodontium, characterized in that it comprises a step of placing a tooth germ tissue-derived or a periodontal membrane tissue-derived cell mass on the entire implant surface or a part thereof which is surrounded by the alveolar bone of the recipient at the time of transplantation of said implant.

Here, one embodiment of the method of the present invention for manufacturing a dental implant that enables the formation of functional periodontium is characterized in that said tooth germ tissue-derived cell mass is a tooth germ mesenchymal tissue-derived or a dental follicle tissue-derived cell mass.

One embodiment of the method of the present invention for manufacturing a dental implant that enables the formation of functional periodontium is also characterized in that said cell mass is derived from tooth germ tissue, and said tooth germ tissue is in any one developmental stage selected from the group consisting of the cap stage, the early bell stage, and the late bell stage.

One embodiment of the method of the present invention for manufacturing a dental implant that enables the formation of functional periodontium is also characterized in that said implant allows orthodontics after implant transplantation.

One embodiment of the method of the present invention for manufacturing a dental implant that enables the formation of functional periodontium is also characterized in that said periodontium formed has at least one characteristic among (i) having functional cementum and functional periodontal membrane, and (ii) having functional nerve fiber.

One embodiment of the method of the present invention for manufacturing a dental implant that enables the formation of functional periodontium is also characterized in that it further comprises, before the step of placing said cell mass, a step of forming a coating layer of a surface coating agent on the entire surface of the implant or a part thereof, wherein the surface is surrounded by the alveolar bone of the recipient at the time of implant transplantation, and that said cell mass is placed on the surface of said coating layer.

One embodiment of the method of the present invention for manufacturing a dental implant that enables the formation of functional periodontium is also characterized in that said surface coating agent is selected from the group consisting of hydroxyapatite, α-tricalcium phosphate, β-tricalcium phosphate, and collagen.

Needless to say, any combination of one or more characteristics of the present invention described above is also a method for manufacturing the dental implant of the present invention.

Moreover, another aspect of the present invention relates to a method for transplanting an implant to a mammal that has lost a tooth, characterized in that it comprises a step of transplanting said implant to said site of tooth loss.

One embodiment of the method of the present invention for transplanting an implant to a mammal that has lost a tooth is also characterized in that said animal is a non-human mammal.

Effects of the Invention

According to the dental implant of the present invention, functional periodontium can be formed around the implant after implant transplantation.

According to the dental implant of the present invention, not only functional periodontium can be formed around the implant after implant transplantation, but regeneration of the alveolar bone around the implant transplantation site can be promoted. Moreover, according to the dental implant of the present invention, the regenerative capacity of the alveolar bone around the implant transplantation site can also be improved.

BRIEF DESCRIPTION OF THE DRAWINGS

FIG. 1A (top row) shows images of a tooth germ resected from a C57/BL/6 mouse at fetal age Day 18 and a natural tooth derived from an adult mouse. FIG. 1B (bottom row) shows images of dental follicle tissue separated from a fetal age Day 18 C57/BL/6 mouse-derived tooth germ and periodontal membrane tissue separated from a natural tooth derived from an adult mouse.

FIG. 2 shows HE staining images of the periodontium on Day 21 after transplantation when dental follicle tissue was transplanted to a periodontal membrane removal model. The HE staining images are stained frontal sections of the jaw bone, and are images viewed in the direction from the incisor to the occipital area. FIG. 2A shows the HE staining image of the control segment without transplantation of dental follicle tissue, and FIG. 2B shows the HE staining image of the segment with transplantation of dental follicle tissue. In the figures, asterisk (*) shows the ankylosis formation site, D shows the dentin, AB shows the alveolar bone, C shows the cementum, and PDL show the periodontal membrane.

FIG. 3 shows a schematic diagram of a transplantation model of an implant with dental follicle tissue pasted on the coating layer of an implant having a coating layer of hydroxyapatite (also called HA) (dental follicle-attached HA implant), which is one embodiment of the present invention. FIG. 3A shows the natural dentition, FIG. 3B shows the tooth extraction of the first molar and gingiva therapy, FIG. 3C shows the creation of a transplantation fossa, and FIG. 3D shows the transplantation of a dental follicle-attached HA implant.

FIG. 4A shows a stereoscopic image (middle left image) of an HA implant with dental follicle tissue wrapped thereto (dental follicle-attached HA implant), which is one embodiment of the present invention, as well as GFP fluorescence images thereof (the middle right image shows an image taken from the side, and the right image shows an image taken from the bottom). A stereoscopic image of an implant (HA implant) having a coating layer of hydroxyapatite before wrapping dental follicle tissue is also shown (left image). FIG. 4B shows CT images of an HA implant and a dental follicle-attached HA implant immediately after transplantation (left image) and on Day 21 after transplantation (middle left, middle right, and right images). The arrow indicates the formation of a periodontal space.

FIG. 5 shows HE staining images of the periodontium after transplantation of a dental follicle-attached HA implant which is one embodiment of the present invention (bottom row), the periodontium of a natural tooth (top row), and the surrounding tissue after HA implant transplantation (middle row). imp indicates the implant.

FIG. 6 shows the stereoscopic image, the GFP fluorescence image, and the merged image of the stereoscopic and GFP fluorescence images for the implant periphery on Day 21 after transplantation, when a GFP mouse-derived dental follicle tissue-attached HA implant which is one embodiment of the present invention is transplanted into the oral cavity (the top image shows the image taken from the side of the lingual side, and the bottom image shows the image taken from the upper jaw side (above)). The arrows indicate the implant.

FIG. 7 shows an azan staining image of the periodontal membrane formed when a dental follicle-attached HA implant which is one embodiment of the present invention was transplanted (right image), and an azan staining image of natural tooth periodontal membrane (left image).

FIG. 8 shows images taken with a scanning electron microscope of the periodontium formed when a dental follicle-attached HA implant which is one embodiment of the present invention was transplanted (bottom row), and the periodontium of a natural tooth (top row).

FIG. 9 shows the image taken with a transmission electron microscope of the periodontium formed when a dental follicle-attached HA implant which is one embodiment of the present invention was transplanted.

FIG. 10 shows images of the distribution of elements: titanium (Ti), calcium (Ca), or phosphorous (P) analyzed with an X-ray microanalyzer (top images in FIG. 10) for the periodontium formed when a dental follicle-attached HA implant which is one embodiment of the present invention was transplanted. The bottom images in FIG. 10 are images showing stereoscopic images corresponding to the image of each analyzed elemental distribution (top image).

FIG. 11 shows images of the distribution of elements: titanium (Ti), calcium (Ca), or phosphorous (P) analyzed with an X-ray microanalyzer, as well as the merged image of distribution images of said three elements, for the periodontium formed when a dental follicle-attached HA implant which is one embodiment of the present invention was transplanted.

FIG. 12 shows a schematic diagram indicating the positional relationship between the incisor and the molar and the implant in an implant transplantation model employed for nerve fiber analysis in periodontal membrane tissue formed after implant transplantation.

FIG. 13A shows merged images of before and after orthodontics in a test of applying orthodontic force to a dental follicle-attached HA implant which is one embodiment of the present invention, a natural tooth, and an HA implant. FIG. 13B shows a graph representing the migration distance of a natural tooth, an HA implant after transplantation, and a dental follicle-attached HA implant after transplantation when orthodontic force was applied.

FIG. 14 shows images of sections analyzed by in situ hybridization for the expression of a bone resorption marker (CSF-1) on the compression side and a osteogenic marker (Ocn) on the tension side on Day 6 after applying orthodontic force to a dental follicle-attached HA implant which is one embodiment of the present invention, a natural tooth, and an HA implant. In the figure, arrows indicate CSF-1 expression sites and arrowheads indicate Ocn expression sites.

FIG. 15 shows images of the periodontal membrane region around a dental follicle-attached HA implant which is one embodiment of the present invention, a natural tooth, and an HA implant when observing the expression of a peripheral nerve marker Neuro Filament (a phase contrast image, a fluorescence image, and a merged image of phase contrast and fluorescence images).

FIG. 16 shows images of sections wherein noxious stimulation was applied by orthodontic force to the periodontal membrane around a dental follicle-attached HA implant which is one embodiment of the present invention, a natural tooth, and an HA implant, and 2 hours later, c-Fos protein expressed in the nucleus tractus spinalis trigemini was analyzed by in situ hybridization. In the figure, arrows indicate the expression sites of c-Fos protein. T indicates the nucleus tractus spinalis trigemini.

FIG. 17, top row, is a schematic diagram showing the steps for creating a three-wall bone defect model. Further, FIG. 17, bottom row, shows a stereophotograph of the three-wall bone defect model, a three-dimensionally constructed micro CT image (three-dimensional CT image), and micro CT images (frontal section and horizontal section). FIG. 17A shows the tooth extraction of the first molar and bone therapy, FIG. 17B shows the creation of the three-wall bone defect, and FIG. 17C shows implant transplantation.

FIG. 18 shows three-dimensional CT images of the alveolar bone of the three-wall bone defect model on the day of transplantation (Day 0), as well as on Day 14, Day 28, and Day 50 from the day of transplantation, when a dental follicle-attached HA implant which is one embodiment of the present invention (bottom row), or an HA implant (middle row) was transplanted to a three-wall bone defect model. Further, FIG. 18, top row, shows three-dimensional CT images of the alveolar bone of a three-wall bone defect model when an implant and the like was not transplanted to a three-wall bone defect model. In the figure, the arrow indicates that the alveolar bone is regenerated to its original height.

FIG. 19 shows micro CT images of the alveolar bone on the day of transplantation (Day 0), as well as on Day 14, Day 28, and Day 50 from the day of transplantation, when a dental follicle-attached HA implant which is one embodiment of the present invention was transplanted to a three-wall bone defect model (top row: sagittal section, middle row: horizontal section, bottom row: frontal section). The arrowheads in the figure indicate a periodontal space-like gap.

FIG. 20 is a graph showing the proportion of the regenerated amount of the alveolar bone on Day 50 from the day of transplantation, when a dental follicle-attached HA implant which is one embodiment of the present invention, or an HA implant was transplanted to a three-wall bone defect model. Further, as a control, the proportion of the regenerated amount of the alveolar bone in a three-wall bone defect model that was not transplanted an implant is shown. One hundred percent in the graph indicates the alveolar bone amount before the alveolar bone defect state.

FIG. 21 shows sagittal cross-sectional images of the alveolar bone on the day of transplantation (Day 0) and Day 50 from the day of transplantation when a dental follicle-attached HA implant which is one embodiment of the present invention (bottom row), or an HA implant (middle row) was transplanted to a three-wall bone defect model. Further, as a control, sagittal cross-sectional images of the alveolar bone on the day of transplantation (Day 0) and Day 50 from the day of transplantation when an HA implant was transplanted to an ordinary alveolar bone without lateral alveolar bone loss (top row) are shown.

FIG. 22 is a graph showing the amount of sinking of the implant into the alveolar bone on Day 50 from the day of transplantation, when a dental follicle-attached HA implant which is one embodiment of the present invention, or an HA implant was transplanted to a three-wall bone defect model. Further, as a control, a graph showing the amount of sinking of the implant into the alveolar bone on Day 50 from the day of transplantation when an HA implant was transplanted to an ordinary alveolar bone without lateral alveolar bone loss.

DESCRIPTION OF EMBODIMENTS

The dental implant according to the present invention is characterized in that it is a dental implant that enables functional periodontium formation, wherein a tooth germ tissue-derived or a periodontal membrane tissue-derived cell mass is placed on the surface of the implant, and the surface of the implant on which the cell mass is to be placed is the whole or a part of the surface which is surrounded by the alveolar bone of the recipient at the time of implant transplantation.

An "implant" is generally an appliance for embedding into a living body used in humans and animals with a medical purpose. An "implant" herein particularly refers to a dental artificial tooth for embedding into the jaw bone instead of a lost tooth.

Any material conventionally employed as an implant material can be used as the implant material used for the present invention, as long as it does not have biotoxicity, has bioaffinity, and is a strong material that may withstand occlusion. Examples of implant materials can include metals, metal alloys, plastic materials, ceramics, composite materials, bone alternative materials, and the like.

In the present invention, examples of metals and metal alloys that may be used as the implant can include titanium, steel, iron, alloy steel, iron alloy, titanium alloy, CoCr alloy, silver, copper, calcium, magnesium, zinc, and the like.

In the present invention, examples of plastic materials that may be used as the implant include polymers such as polyethylene, polypropylene, polytetrafluoroethylene, polyethylene terephthalate, polyamides, polyurethanes, polysiloxanes, polysiloxane elastomers, polyether ether ketones, polysulfones, polysaccharides, and polylactides.

In the present invention, ceramic materials that may be used as the implant include, e.g., oxides such as aluminum oxide, zirconium oxide, titanium oxide, and silicon oxide or nitrides, e.g., calcium phosphate such as hydroxyapatite, glass and glass ceramics, preferably glass and glass ceramics that dissolve or degrade under a physiologic condition, and the like.

The material used for the implant of the present invention is more preferably titanium or a titanium alloy with respect to biocompatibility or mechanical biocompatibility. Examples of bone alternative materials include an autologous tooth, a tooth obtained from an allogeneic individual, and a tooth obtained from a heterologous individual.

The form and size of the implant used for the present invention can be appropriately designed by those skilled in the art according to the tooth loss site to be transplanted.

Moreover, in one embodiment of the present invention, the dental implant can have a coating layer of a surface coating agent formed on the surface thereof.

A "surface coating agent" herein is those used in the formation of scaffold when adhering a cell mass to an implant. The coating layer of a surface coating agent formed on the implant surface can improve the adherence of the cell mass to the implant.

Examples of the surface coating agent used for the present invention can include gel materials such as hydroxyapatite, α-TCP (tricalcium phosphate), β-TCP, or collagen.

In particular, hydroxyapatite has a biological activity to promote osteogenesis, and can promote cementum formation around the implant after implant transplantation or implant engraftment to the bone. In such respects, hydroxyapatite is preferably used as the surface coating agent.

Those having an effect similar to a surface coating agent can be used as the implant material of the present invention, such as for example use of hydroxyapatite. In this case, a tooth germ tissue-derived or a periodontal membrane tissue-derived cell mass can be placed directly on the implant surface deeming that the implant already has a layer equal to a coating layer of a surface coating agent. Alternatively, a surface coating agent that is different from the implant material can also be further coated on the implant surface, and the cell mass further placed on the surface thereof.

The surface coating agent can be coated so that it covers the whole or a part of the surface of the implant, wherein the surface is surrounded by the alveolar bone of the recipient at the time of implant transplantation. Moreover, the coating layer of a surface coating agent is formed so that it lies between the implant and the cell mass to be placed on the implant.

On the surface (which is) surrounded by the alveolar bone of the recipient at the time of implant transplantation refers to a part on the surface of the implant that is buried into the tooth loss site of the recipient immediately after implant transplantation. This portion will be connected to the periodontium of the recipient in the future.

The coating method of the surface coating agent can be performed by a method well-known to those skilled in the art.

For example, when coating hydroxyapatite to the implant, this can be performed by vapor deposition, plasma spraying method, and the like. The thickness of the surface coating agent layer or the coating range of the surface coating agent can be appropriately set by those skilled in the art according to the implant subject to coating or the site of loss to be transplanted. In one embodiment of the present invention, the thickness of the coating layer can be e.g. 1 µm-2 µm.

In addition to forming a coating layer of a surface coating agent on the implant surface as described above, a commercially available implant which has a surface coating agent such as hydroxyapatite already coated thereon can also be used.

"Periodontium" refers to the tissue composed of the cementum, the periodontal membrane, the alveolar bone, and the gingiva formed mainly on the outer layer of a tooth. The periodontium formed by transplantation of the implant of the present invention is in particular the cementum, the periodontal membrane, and the alveolar bone. The cementum and the periodontal membrane that are formed after transplantation of the implant of the present invention form the periodontium by connecting to the recipient's alveolar bone or gingiva and the like.

The cementum, the periodontal membrane, and the alveolar bone can be easily morphologically specified by tissue staining. For example, an ordinary hematoxylin/eosin (HE) staining can be used as the staining method. In order to perform tissue staining, those skilled in the art can perform HE staining after e.g. the steps such as fixing the sample with 4% paraformaldehyde (Paraformaldehyde: PFA), decalcifying with 10% ethylenediaminetetraacetic acid (EDTA), embedding in paraffin, and then preparing serial sections at a thickness of 10 micrometers. In addition to the above exemplification, those skilled in the art will be able to perform tissue staining according to a general method to make a histological evaluation.

A "tooth germ" herein is an early tooth embryo that is destined to become a tooth in the future, and refers to those in the bud stage, the cap stage to the bell stage generally employed in the developmental stage of the teeth, in particular tissue in which accumulation of dentin and enamel characteristic of hard tissues of teeth is not observed.

In one aspect of the present invention, a tooth germ in the cap stage, the early bell stage, and the late bell stage can be used as the tooth germ tissue that may be used for the present invention. These tooth germs in the cap stage, the early bell stage, and the late bell stage are preferred in that they have a high potential of being differentiated into functional periodontium when transplanted together with an implant. In particular, the use of a tooth germ in the early bell stage is more preferred. An early bell stage tooth germ-derived cell mass is preferred in that it can further promote the formation of the cementum that accompanies the formation of functional periodontium.

In a mouse, for example, fetal age 13-15 days corresponds to the cap stage, fetal age 16-18 days corresponds to the early bell stage, and fetal age 19 days—after birth corresponds to the late bell stage.

A "regenerated tooth embryo" artificially formed by a cell culture technology can also be employed as the tooth germ that may be used for the present invention. The cell mass can also be collected at the preferred developmental stage when using a regenerated tooth embryo. The regenerated tooth embryo used for the present invention may be those prepared by any method, and can be for example prepared by a method comprising a step of placing a first cell aggregate composed substantially of mesenchymal cells and a second cell aggregate composed substantially of epithelial cells in close contact, and a step of culturing the first and second cell aggregates inside a support carrier.

Examples of a method for manufacturing a regenerated tooth embryo are described in International Publication No. 2006/129672, Japanese Patent Publication (Kokai) No. 2008-29756, Japanese Patent Publication (Kokai) No. 2008-206500, Japanese Patent Publication (Kokai) No. 2008-200033, Japanese Patent Publication (Kokai) No. 2008-29757, International Publication No. 2011/056007, and International Publication No. 2011/056008, the disclosures of each of which are incorporated herein by reference in their entireties.

The tooth germ and other tissues can be collected from the jaw bone or the periodontium and the like of mammals like primates (such as humans, monkeys), ungulates (such as pigs, cows, horses), small mammals like rodents (such as mice, rats, rabbits), as well as various animals such as dogs and cats. For the collection of the tooth germ and tissue, as well as the separation of tissue from the tooth germ, ordinarily, conditions employed for tissue collection may be directly applied to remove them in a sterile state and store in a suitable preservation solution. Human tooth germs can include the tooth germ of the third molar, the so-called wisdom tooth, as well as a fetal tooth germ, but it is preferred to employ the tooth germ of the wisdom tooth with respect to utilizing autologous tissue.

A "cell mass" herein refers to a tooth germ tissue-derived or a periodontal membrane tissue-derived cell mass to be placed on the surface of the implant. In addition, a cell mass also refers to the whole of the tissue from which it is derived or a part thereof which at least partially maintains the functional binding between cells that form the tissue.

The tooth germ tissue-derived cell mass that may be used for the present invention includes a tooth germ mesenchymal tissue, a dental follicle tissue, and the like. The tooth germ mesenchymal tissue exists in a tooth germ in the bud stage, the cap stage, or the early bell stage. Moreover, dental follicle tissue exists in a tooth germ in the early bell stage and the late bell stage. Moreover, the periodontal membrane tissue used for the present invention can be collected from a complete tooth. For the separation of tissues such as tooth germ mesenchymal tissue and dental follicle tissue from tooth germ tissue, and the separation of periodontal membrane tissue from a complete tooth, ordinarily, conditions employed for tissue collection may be directly applied to remove them in a sterile state and store in a suitable preservation solution. In this case, an enzyme may be employed to facilitate separation. Examples of an enzyme can include dispase, collagenase, and trypsin.

The cell mass can also be used by physically cutting tissue resected from a living body into several cell masses. In such a case, the cell mass is preferably cut so that the functional binding between cells upon the formation of the tissue is partially retained. In particular, it is preferred that the cell mass after cutting retains the form that will allow discrimination between the exterior and the interior of the tissue. As such, the cell mass used for the present invention enables the formation of periodontium having normal function when transplanted together with an implant by partially retaining the functional binding between cells upon the formation of the tissue. The form of the cut cell mass is not particularly limited as long as it has a form that facilitates it being placed on the surface of the implant, and for example can be cut into long narrow shapes as with strips. For such cutting of a cell mass, ordinarily, conditions employed for tissue collection may be directly applied.

The method for placing a cell mass on an implant surface is not particularly limited. For example, the cell mass cut into strips can be pasted on the implant surface so that the cell mass will not overlap each other. Alternatively, they can also be placed by wrapping the cell mass on the implant surface so that they will not overlap each other. At this point, adhesiveness will improve if the implant with a cell mass pasted thereon is dried a little in air. When there is a coating layer of a surface coating agent on the implant surface, the cell mass can be placed on the further surface of the coating layer of a surface coating agent.

In one aspect of the present invention, the position for placing the cell mass on the implant surface can be allocated on the whole or a part of the surface that will be surrounded by the alveolar bone of the recipient after implant transplantation. It is also preferred that the implant is placed to a range that will be implanted into the alveolar bone of the recipient. It is also preferred that the side of the cell mass that had formed the tissue interior is placed contacting the implant surface. By such placement, the side that had formed the tissue exterior will be facing the alveolar bone of the recipient.

In the present invention, for example, an implant having a dental follicle cell placed thereon is referred to as a dental follicle-attached implant.

Moreover, another aspect of the present invention provides a method for transplanting an implant, comprising a step of implanting an implant manufactured by the method for manufacturing an implant according to the present invention into a tooth loss site.

According to the implant according to the present invention, functional periodontium can be formed around the implant after implant transplantation.

In the method of the present invention for transplanting an implant into a tooth loss site in the oral cavity, it is preferred that in the tooth germ tissue-derived or a periodontal membrane tissue-derived cell mass to be placed on the implant, the side that had formed the tissue interior is in contact with the surface of the implant. By doing so, the side that had formed the tissue exterior will be placed facing the periodontium of the recipient. As such, by approximating the tooth germ tissue-derived or the periodontal membrane-derived cell mass to the state it exists in the periodontium of an actual natural tooth, the formation of functional periodontium can be promoted.

Site of loss means a portion created in the gingiva by tooth extraction and the like, and is not restricted in form. The position of loss and the type of tooth of interest are not particularly limited as long as the implant of the present invention is buriable.

The site of loss is ordinarily located in the jaw bone, the alveolar bone of the oral cavity, and the like. Moreover, if the alveolar bone amount is reduced due to tooth loss, a well-known method that is clinically employed for burying an implant such as the GTR method (guided tissue regeneration) may be performed on the site of loss to thereby regenerate bone and increase bone mass. After placement to the site of loss to be the implant target, suturing etc. is preferably performed according to ordinary treatments.

In order to prevent the cell mass attached on the implant surface from being peeled off from the surface when transplanting the implant to the site of loss, a site of loss having a diameter that is slightly larger than the implant diameter can also be surgically formed. When an implant is transplanted to such a site of loss having a large diameter, the space between the implant after transplantation and the alveolar bone of the recipient will be filled with blood from surrounding tissue.

In the method for transplanting an implant according to the present invention, the transplantation subject is preferably allogeneic to the animal from which the tooth germ tissue or the periodontal membrane tissue for manufacturing the implant was resected, and further preferably an individual identical to the individual from which the tooth germ tissue or the periodontal membrane tissue was resected. The animal can include mammals including humans, cows, horses, pigs, dogs, cats, mice, and the like. A non-human mammal is also preferred.

The implant transplantation site can be morphologically easily observed by those skilled in the art by visual observation or CT imaging and the like. A CT image or a CT section image can also be easily photographed by employing an appliance well-known to those skilled in the art. For CT tomography, 3D micro X-ray CT R_mCT for experimental animals (Rigaku) and the like can be employed under conditions such as 90 kV, 150 mA, tomography thickness 10 mm, and the like. Moreover, those skilled in the art can perform image construction and analysis etc. after CT tomography by employing an appropriate image analysis software. Examples of image analysis softwares that can be employed are image filing software i-VIEW Type R for small animals and high resolution 3D/4D image analysis software Imaris (Bitplane). Moreover, in addition to the above exemplification, it will be possible for those skilled in the art to perform CT tomography and analysis by employing a similar appliance and setting appropriate conditions and by utilizing a similar image analysis software.

According to the implant of the present invention, functional periodontium can be formed around the implant after transplantation to a recipient. In the present invention, functional periodontium refers to those (i) having functional cementum and functional periodontal membrane or (ii) having functional nerve fiber, preferably those having both characteristics of (i) and (ii).

In other words, functional periodontium can be evaluated by e.g. whether it has functional cementum and functional periodontal membrane. Functional cementum and functional periodontal membrane can be evaluated by e.g. verifying whether it has a layered structure equivalent to that of the periodontium of a natural tooth when subject to histological analysis by HE staining, azan staining, and the like. Here, the periodontal membrane of a natural tooth ordinarily has periodontal membrane fibers running vertically to the longitudinal direction of the tooth root. This periodontal membrane has an important role particularly in supporting the occlusal force of teeth. Accordingly, the function of periodontal membrane in particular can be evaluated by analyzing whether periodontal membrane fibers running vertically to the longitudinal direction of the implant are formed similarly to a natural tooth. For the morphological analysis of periodontium or the analysis of the running of periodontal membrane, for example, its morphology can also be observed by a scanning electron microscope or a transmission electron microscope in addition to the above method. In order to verify the three-layer structure of hard tissue-fibrous tissue-hard tissue in the periodontium, the layered structure of the periodontium can be verified for example by analyzing the elemental distribution with an X-ray microanalyzer.

As another method, the function of bone remodeling against orthodontic force loading can be evaluated as described in Example 4 below. The evaluation can also be performed by analyzing whether or not the implant after transplantation is migratable by orthodontic force loading. For evaluation of bone remodeling, for example, evaluation can be performed by analyzing the expression of an osteogenic marker and/or a bone resorption marker after orthodontic force loading. The periodontium formed when the implant of the present invention is transplanted, upon application of an orthodontic force equivalent to that of a natural tooth, has 68% or more movement, preferably has 80% or more migration compared to a natural tooth.

The functional periodontium can also be evaluated by for example whether or not it has functional nerve fiber. Functional nerve fiber refers to nerve fiber that can transmit the stimulation when stimulation etc. is applied to the periodontium. Whether or not the nerve fiber is functional can be evaluated for example as in the method described in Example 6 below by applying stimulation by orthodontic force loading to the periodontium of the evaluation subject, and then analyzing the expression of c-fos in the trigeminal tract nucleus.

Moreover, according to the dental implant of the present invention, not only the formation of functional cementum or periodontal membrane can be promoted, but the regeneration of the alveolar bone can be promoted, and the regenerative capacity of the alveolar bone can be improved. "Improve the regenerative capacity of the alveolar bone" as used herein refers to the fact that by transplanting the dental implant according to the present invention to a transplantation site that is missing a portion of the alveolar bone, the alveolar bone is able to regenerate so that it is more approximated to the pristine form of the alveolar bone compared to when a conventional implant was transplanted or when an implant was not transplanted. On account of this, the dental implant according to the present invention can prevent situations such as the implant after transplantation gradually sinking into the alveolar bone due to partial loss of the alveolar bone, and enables maintenance of the position (such as height) or direction of the transplanted implant and the like.

The terms used herein are employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having consistent meanings with the meanings herein and in related technical fields, and shall not be construed as having idealized or excessively formal meanings.

The embodiments of the present invention may be described with reference to schematic diagrams. In case of schematic diagrams, they may be exaggerated in presentation in order to allow clear description.

Terms such as first and second are employed to express various elements, and it should be recognized that these elements are not to be limited by these terms. These terms are employed solely for the purpose of discriminating one element from another, and it, is for example possible to describe a first element as a second element, and similarly, to describe a second element as a first element without departing from the scope of the present invention.

In the present specification, unless clearly expressed otherwise, any and all numeric values employed for indicating a numeric value range and the like is construed as encompassing the meaning of the term "about." For example, unless clearly expressed otherwise, "10-folds" is understood to mean "about 10-folds."

The literatures referenced herein should be deemed that the disclosures of all of which are cited herein, and those skilled in the art shall cite and recognize the related disclosure contents in these prior art literatures as a part of the present specification according to the context herein without departing from the spirit and the scope of the present invention.

The present invention will now be described in further detail with reference to Examples. However, the present invention can be embodied by various aspects, shall not be construed as being limited to the Examples described herein.

EXAMPLES

Example 1

Analysis of Periodontium-Forming Ability by Transplantation of Dental Follicle Tissue in Periodontal Membrane Removal Model (Preparation of Dental Follicle Tissue)

The dental follicle tissue in this experiment was obtained from a C57/BL/6 mouse at fetal age Day 18 in the bell stage. Specifically, dental follicle tissue was separated from a tooth germ that will become the mandibular first molar. The resection of the tooth germ was performed according to the method of Nakao et al. (Nakao K, et al. Nat Methods. 2007; 4(3): 227-30).

The method of resecting dental follicle tissue from the resected tooth germ at fetal age Day 18 was performed as follows. The tooth germ was washed twice with PBS(−) (phosphate-buffered saline) containing $Ca^{2+}$ and $Mg^{2+}$, and then subjected to an enzyme treatment with 100 U/ml collagenase I (Worthington, Lakewood, N.J.) at room temperature for 2 minutes. The tissue was then physically separated in 10% Fetal calf serum (FCS; Hyclone, Logan, Utah) comprising 20 U/ml DNase I (TAKARA BIO, Shiga, Japan), and Dulbecco's modified eagle medium (D-MEM; WAKO, Osaka, Japan) supplemented with 100 U/ml penicillin and 100 mg/ml streptomycin (SIGMA, St. Louis, Mo.) with a 25 G needle (NN-2516R, TERUMO, Tokyo, Japan). The dental follicle tissue separated from mouse tooth germ at fetal age Day 18 had a saccular morphology (see FIG. 1).

(Preparation of Periodontal Membrane Removal Model and Transplantation of Dental Follicle Tissue)

In order to analyze the periodontium-forming ability at the periodontal membrane removal site, periodontal membrane of the second molar of a 4 weeks-old C57BL/6 mouse was removed according to the method of Saito et al. (Saito M, et al. J Biol Chem. 2011; 286 (44), 38602-13.) (periodontal membrane removal model). More specifically, in a mouse under deep anesthesia, the mandibular first molar was extracted for convenience purposes due to a procedural issue. The periodontal membrane on the buccal side of the second molar was then physically removed from the alveolar septum between the first molar and the adjacent second molar with a 25 G needle (NN-2516R, TERUMO, Tokyo, Japan).

The dental follicle tissue separated from mouse tooth germ at fetal age Day 18 was physically cut into multiple cell mass strips. Next, these were transplanted by pasting to the periodontal membrane removal site so that the side of the cell mass that had formed the dental follicle tissue interior faces the second molar tooth root side where the periodontal membrane was removed. At this time, pasting to the periodontal membrane removal site was carried out so that each cell mass would not overlap. The jaw bone was resected on Day 21 after transplantation, and tissue analysis of the dental follicle tissue transplantation site was performed by HE staining.

In the control segment without transplantation of dental follicle tissue, ankylosis in which a large portion of periodontal membrane tissue at the site where periodontal membrane was removed is filled with bone-like tissue had occurred (asterisk in FIG. 2A). In contrast, normal cementum and periodontal membrane were formed in the segment with transplantation of dental follicle tissue. Periodontal membrane tissue that runs vertically to the longitudinal direction of the tooth root was also observed in the group with transplantation of dental follicle tissue, and a periodontium structure equivalent to that of a natural tooth was formed (FIG. 2A and FIG. 2B). From this, it was shown that dental follicle tissue enables the formation of all tissues of periodontium composed of the cementum, the periodontal membrane tissue, and the alveolar bone, and also enables the formation of periodontium even at the site of periodontal membrane damage.

Example 2

Evaluation of Periodontium-Forming Ability by Transplantation of Dental Follicle Tissue-Attached Implant (Preparation of Implant)

The implant form for transplantation was prepared by cutting a 1.7 mm length of titanium wire having a diameter of 0.6 mm (The Nilaco Corporation, Tokyo, Japan), and forming it into a shape of a circular cone at about 0.5 mm from the side which will be the root apex direction. The surface of the implant form was coated with hydroxyapatite by vacuum deposition, and covered with a layer of hydroxyapatite having a thickness of 2 μm to thereby prepare an implant form coated with hydroxyapatite (hereinafter an HA implant) (YAMAHACHI DENTAL MFG., CO., Aichi prefecture, Japan).

Dental follicle tissue resected from a C57BL/6 mouse at fetal age Day 18 was wrapped around the HA implant by a method similar to Example 1 (hereinafter a dental follicle-attached HA implant; FIG. 4A). The dental follicle tissue used was those surgically cut into several cell mass strips. The placement of the cell mass on the HA implant was carried out by wrapping it so that the cell masses will not overlap each other. Moreover, the side of the cell mass that had formed the dental follicle tissue interior was adhered to the surface of the HA implant.

(Transplantation of Dental Follicle-Attached HA Implant to Jaw Bone and Evaluation of Survival)

The mandibular first molar of a 4 weeks-old C57BL/6 mouse was extracted to establish a tooth loss site, and 4-5 days of gingiva healing period was allowed. Gingiva incision/detachment at the tooth extraction site of the mandibular first molar was then carried out. A dental micromotor (Viva-Mate Plus, NSK, Tokyo, Japan) and a dental reamer (MANI, Tochigi, Japan) were employed to cut the alveolar bone at the site of tooth loss, and a transplantation fossa having a diameter of 0.9 mm and a depth of 1.2 mm was formed. A dental follicle-attached HA implant prepared as above was transplanted to the transplantation fossa. A control segment with transplantation of an HA implant without dental follicle tissue wrapped thereto was also prepared. The gingiva at the implant transplantation site was sutured with an 8-0 nylon surgical suture (BEAR Medic, Chiba, Japan) (FIG. 3). The mouse with transplantations of each implant form was subjected to micro CT tomography immediately after transplantation and on Day 21 after transplantation (In vivo Micro X-ray CT System; R_mCT, Rigaku Corporation, Tokyo, Japan). For the image data, the connection between the implant and the alveolar bone of the recipient was evaluated over time with an integrated image processing software (i-VIEW-3DX, Morita Corporation, Osaka, Japan). Moreover, on Day 21 after transplantation, the jaw bone comprising the implant was resected from the recipient mouse and subjected to histological evaluation by HE staining.

On Day 21 after transplantation, the control segment with transplantation of an HA implant showed osseointegration in which the alveolar bone was directly connected to the surface layer of the implant (FIG. 4B and FIG. 5). In contrast, in the case of a dental follicle tissue-attached HA implant, periodontal space was observed between the surface layer of the implant and the surrounding alveolar bone (arrow in the bottom row, middle right image of FIG. 4B). Moreover, in the case of a dental follicle tissue-attached HA implant, a tissue structure equivalent to that of the periodontium of a natural tooth such as the cementum, the periodontal membrane, and the alveolar bone from the surface layer of the implant was observed in the HE staining image (FIG. 5).

Further, in order to verify whether the periodontium formed is derived from the periodontium that is transplanted together with the implant, a GFP mouse (C57BL/6-Tg (CAG-EGFP) mouse (Japan LSC, Inc., Japan))-derived dental follicle tissue-attached HA implant form was similarly prepared and transplanted, and the transplantation site was observed. GFP coloring of the transplantation site was photographed with a fluorescence stereomicroscope (Axio-Lumer, Carl Zeiss, Jene, Germany). As a result, the formation of GFP mouse-derived tissue was observed on Day 21 at the periodontal membrane and the alveolar bone region around the implant (FIG. 6). From this, a possibility was shown that by transplanting a dental follicle tissue-attached implant, it had survived on the jaw bone of the recipient accompanied by periodontium formation.

Example 3

Analysis of Periodontium Formed after Implant Transplantation

As shown in Example 2, transplantation of a dental follicle-attached HA implant allowed formation of periodontium that had survived on the jaw bone. Accordingly, in order to analyze the running of the periodontal membrane formed after transplanting the dental follicle-attached HA implant, the periodontium of a natural tooth, the periodontium surrounding the implant on Day 21 after transplantation of a dental follicle-attached HA implant, and the periodontium surrounding the implant on Day 21 after transplantation of an HA implant without dental follicle tissue wrapped thereto were stained by azan staining, and the running of periodontal membrane was analyzed.

Moreover, in order to analyze the morphology of the periodontium formed after transplanting the dental follicle-attached HA implant, the periodontium surrounding the implant on Day 28 after transplantation of a dental follicle-attached HA implant was observed by a scanning electron microscope and a transmission electron microscope, and the morphology of the periodontium formed after implant transplantation was analyzed.

Further, in order to verify whether the three-layer structure of hard tissue-fibrous tissue-hard tissue was formed in the periodontium formed after transplanting the dental follicle-attached HA implant, elemental distribution analysis of titanium (Ti), calcium (Ca), and phosphorous (P) with an X-ray microanalyzer was performed for the periodontium surrounding the implant on Day 28 after transplantation of a dental follicle-attached HA implant.

(Analysis of Periodontal Membrane Running by Azan Staining)

Using a method similar to Example 2, a dental follicle-attached HA implant was transplanted to the site of mandibular first molar loss of a 4 weeks-old C57BL/6 mouse. The jaw bone was resected on Day 21 after transplantation, and the jaw bone was fixed in 4% paraformaldehyde solution for 24 hours. Decalcification operation was then performed for 72 hours with 10% formic acid sodium citrate and 22.5% formic acid decalcification solution. After the decalcification operation, the jaw bone was embedded in paraffin. After embedding, 6 µm thick sections were prepared from the jaw bone with a cryostat (CM3050S; Leica microsystems).

Next, the paraffin sections prepared to a thickness of 6 µm were immersed in xylene for 6 minutes. Each of these was then immersed in 100%, 90%, and 70% alcohol for 3 minutes each to remove the paraffin. Flowing water was poured on the sections with the paraffin removed for 5 minutes in order to get it accustomed to water, and this was then immersed in 10% trichloroacetic acid/10% potassium dichromate for 15 minutes. Flowing water was again poured on the sections, and this was then immersed in azocarmine G solution for 30 minutes to stain the nucleus and the cytoplasm. Azocarmine G solution was washed with flowing water, this was then immersed in aniline/alcohol for 10 seconds for differentiation, and immersed in acetic acid alcohol for 1 minute to stop the differentiation. After stopping the differentiation, the sections were washed with flowing water, and immersed in 5% phosphotungstic acid for 1 hour. After immersion, this was again washed with flowing water, and then immersed in aniline blue/orange G mixed solution for 10 minutes to stain periodontal membrane fiber. Finally, differentiation was performed with 100% alcohol, and this was immersed in xylene for 6 minutes for clarification. This was then sealed with marinol and tissue analysis was carried out.

The periodontal membrane tissue formed around the implant on Day 21 after transplantation of a dental follicle-attached HA implant had a running direction vertical to the longitudinal direction of the implant as with the running of the periodontal membrane of a natural tooth (FIG. 7).

(Morphological Analysis by Electron Microscope)

Using a method similar to Example 2, a dental follicle-attached HA implant was transplanted to the site of mandibular first molar loss of a 4 weeks-old C57BL/6 mouse. On Day 28 after implant transplantation, the mouse was placed under deep anesthesia and subjected to transcardial perfusion fixation with Karnovsky fixing solution. After transcardial perfusion fixation, the jaw bone of the mouse was resected, and then the jaw bone was postfixed under 4° C. condition with 31% osmium tetrachloride. Next, the jaw bone was dehydrated with ethanol, then dried in a critical point dryer (HCP-2, HITACHI, Tokyo, Japan), and substituted with and embedded in epoxy resin.

A portion of the sample embedded in epoxy resin was cut in sagittal section with a diamond disc so that the center of the transplanted implant will be the cutting plane. The cut sample was subjected to a conductive treatment with an ion sputtering device (E-1030, HITACHI) and an Au—Pd vapor deposition treatment. The Au—Pd vapor-deposited sample was then observed with a scanning electron microscope (S-4700, HITACHI) with the acceleration voltage at 5 kV. Similarly to the method above, a sample was also prepared from another C57BL/6 mouse for a natural tooth, and the morphology of the periodontium of a natural tooth was observed by a scanning electron microscope.

Moreover, for a portion of the sample after epoxy resin embedding prepared from a mouse with transplantation of a dental follicle-attached HA implant, ultra-thin sliced sections of 100 nm were prepared with an ultramicrotome (ULTRACUT-UCT; Leica microsystems). The prepared sections were observed with a transmission electron microscope (H-7600, HITACHI) with the acceleration voltage at 75 kV.

A scanning electron microscope (SEM) image of the periodontium surrounding the implant on Day 28 of transplantation of a dental follicle-attached HA implant was obtained as described above and observed. As a result, a dense periodontal membrane fiber bundle that runs from the surface layer of the implant towards the alveolar bone and the formation of a lamellar cementum were observed in the SEM image, and tissue morphology almost similar to a natural tooth was recognized (FIG. 8). Moreover, in an SEM image observing the periodontium surrounding the implant after implant transplantation, the connection between the surface layer of the implant and the periodontal membrane fiber was observed (FIG. 8, bottom row). Moreover, in a transmission electron microscope (TEM) image observing the periodontium surrounding the implant after implant transplantation, the connection between the cementum and the periodontal membrane fiber was also observed (arrows in FIG. 9)

(Elemental Analysis by X-ray Microanalyzer)

In order to more clearly analyze the three-layer structure of hard tissue-fibrous tissue-hard tissue in the periodontium surrounding the implant after transplantation of a dental follicle-attached HA implant, analysis of elemental distribution with an X-ray microanalyzer was performed. Titanium (Ti) which is a constituent element of the implant, calcium (Ca) which is a constituent element of the bone tissue and the cementum, and phosphorous (P) were selected as analysis target elements, and elemental distribution of each was analyzed. Moreover, for the analysis of elemental distribution, the distribution of the above three elements were analyzed for the same mouse-derived sample as that used in the above scanning electron microscope analysis (sample embedded in epoxy resin and cut in sagittal section with a diamond disc) with an electron beam microanalyzer (EPMA-1610, Shimadzu Corporation, Kyoto, Japan).

From the analysis result, distribution of Ca and P was seen on the surface layer of the implant made from titanium (FIG. 10). Since the thickness of the hydroxyapatite coating on the implant surface is extremely thin at 2 µm or less, this distribution of Ca and P on the surface layer of the implant is thought to be derived from the cementum that comprises Ca and P as constituent elements. Accordingly, it became clear that a hard tissue consisting of the cementum was formed on the surface layer of the implant. Moreover, in the SEM image of the periodontium surrounding the implant after implant transplantation, distribution of Ca and P was not observed in the portion where the fibers are running. Since periodontal membrane does not comprise Ca and P as constituent elements, it became clear that the periodontal membrane region was reserved in the portion where distribution of Ca and P was not observed.

Moreover, by merging the distribution images of each constituent element and more clearly observing the distribution of the three elements, a spot where Ca and P accumulates could be confirmed on the implant surface (on Ti surface) (FIG. 11).

Example 4

Functional Analysis of Periodontal Membrane Formed after Implant Transplantation In order to analyze the function of the periodontal membrane formed after transplanting the dental follicle-attached HA implant, experimental orthodontic movement was performed on a natural tooth, the dental follicle-attached HA implant on Day 21 after transplantation, and the HA implant without dental follicle tissue wrapped thereto on Day 21 after transplantation, and the migration amounts of the tooth and implants over time were measured. Moreover, as analysis of bone remodeling by experimental orthodontic movement, the expression of a bone resorption marker and an osteogenic marker in the periodontium after orthodontic force loading was analyzed.
(Experimental Orthodontic Movement of Implant)

The methods for analyzing the experimental orthodontic movement of the natural tooth and the implants and the migration amounts of the natural tooth and the implants due to orthodontic force loading were performed as follows. Similarly to the method of Example 2, a dental follicle-attached HA implant or an HA implant were each transplanted to a C57/BL/6 mouse. The mouse was fixed under deep anesthesia on Day 21 after transplantation. A nickel-titanium wire (VIM-NT, Oralcare Co., Ltd. Tokyo, Japan) having a diameter of 0.010 inches was resin-fixed to the mandibular incisor and the natural tooth or the implant to be the subjects of orthodontic movement. With a dial tension gauge (Mitutoyo), a load of 10 g-15 g was horizontally loaded. The orthodontic force was applied to the natural tooth, the HA implant, and the dental follicle-attached HA implant from the lingual to buccal direction (direction vertical to the side of the dentition and towards the oral cavity exterior) for 14 days.

Note that the mandibular incisor of a mouse grows in the anterior direction of the jaw bone, and the molar erupts in the upward direction. The transplanted implant is transplanted on the molar side (FIG. 12). Micro CT tomography was carried out before orthodontic movement, Day 3 after orthodontic movement, Day 7, and Day 14 after orthodontic movement. The migration distance over time due to orthodontic force was measured for the photographed image data with TRI/3D-BON software (Ratoc, Osaka, Japan).

The result is shown in FIG. 13. Migration of the implant due to orthodontic force loading was not observed for the HA implant without dental follicle tissue wrapped thereto. In contrast, a migration of 77.0±5.5 µm was observed with the natural tooth up to Day 7 from orthodontic force loading. For the dental follicle-attached HA implant, a migration of 55.6±6.3 µm was observed up to Day 7 from orthodontic force loading. For the natural tooth and the dental follicle-attached HA implant, gentle tooth migration was observed on Day 7 and after (FIG. 13A and FIG. 13B).
(Expression Analysis of Bone Resorption Marker and Osteogenic Marker after Orthodontic Force Loading)

Next, bone remodeling of the implant transplantation site by experimental orthodontic movement was analyzed. As the method for analyzing bone remodeling, expression analysis of Colony stimulating factor 1 (CSF-1) which is a bone resorption marker and Osteocalcin (OCN) which is a osteogenetic marker was carried out.

Specifically, primers capable of specifically amplifying the gene sequences of OCN and CSF-1 were first designed from the mRNA sequence information disclosed in GenBank. The T7 RNA polymerase promoter sequence was added to these primers, and the target sequences were amplified by PCR. The PCR product obtained as well as T7 RNA polymerase and digoxigenin (DIG) RNA Labeling Mix (Roche, Mannheim, Germany) were employed to synthesize DIG-labeled RNA probes.

Next, experimental orthodontic movement of the natural tooth and the implants was carried out similarly to the previously described method, and the jaw bone was resected on orthodontic movement Day 6. After fixing the resected jaw bone in 4% paraformaldehyde solution for 24 hours, decalcification operation was performed for 72 hours with 10% formic acid sodium citrate and 22.5% formic acid decalcification solution. The jaw bone was then immersed in each of 12.5% (w/v) and 25% (w/v) sucrose solutions in order for 12 hours each, and freeze-embedded with OCT compound (Miles Inc, Naperville, Ill.). After embedding, the jaw bone was prepared into 10 µm thick sections with a cryostat (CM3050S; Leica microsystems).

After preparing frozen sections having a thickness of 10 µm, the frozen sections were fixed for 10 minutes by 4% paraformaldehyde solution treatment, and immersed for 1 minute in an acetylation solution. After 1 hour of prehybridization, the previously synthesized RNA probes were hybridized at 70° C. for 16 hours. The localization of mRNA was detected by enzyme coloring at 30° C. for an appropriate time by an immunological means employing alkaline phosphatase-labeled anti-DIG Fab Fragments and NBT/BCIP (Roche, Mannheim, Germany).

The primers employed in the test are shown below.

```
mouse osteocalcin (mOCN), forward primer
                                    (SEQ ID NO. 1)
TAGCAGACACCATGAGGACC mouse osteocalcin (mOCN), reverse primer
                                    (SEQ ID NO. 2)
TGACATCCATACTTGCAGGG mouse CSF1 (mCSF1), forward primer
                                    (SEQ ID NO. 3)
TACTGAACCTGCCTGCTGAA mouse CSF1 (mCSF1), reverse primer
                                    (SEQ ID NO. 4)
CCAGAGCTTGTGACAGGACA
```

As a result, the localization of osteoclasts that express CSF-1 mRNA was observed on the compression side, and the localization of osteoblasts that express OCN mRNA was observed on the tension side (FIG. 14). From this, it was shown that an HA implant with dental follicle tissue wrapped thereto had formed periodontium which has a function that enables tooth migration.

Example 5

Analysis of Nerve Fiber in Periodontal Membrane Tissue Formed after Implant Transplantation Peripheral nerves penetrate the periodontal membrane tissue of a natural tooth for tooth function and maintenance of homeostasis, and are responsible for a function by afferent stimulus transmission. Accordingly, it was evaluated whether or not nerve fibers having normal function were also formed in the periodontal membrane tissue surrounding the HA implant on Day 21 after transplantation and the dental follicle-attached HA implant on Day 21 after transplantation.

First, similarly to the method of Example 2, a dental follicle-attached HA implant and an HA implant were transplanted to a C57/BL/6 mouse. Then, on Day 21 after transplantation, the jaw bone comprising the dental follicle-attached HA implant or the HA implant was resected from the recipient mouse. After fixing the resected jaw bone in 4% paraformaldehyde solution for 24 hours, decalcification operation was performed for 72 hours with 10% formic acid sodium citrate and 22.5% formic acid decalcification solution. The jaw bone was then immersed in each of 12.5% (w/v) and 25% (w/v) sucrose solutions in order for 12 hours each, and freeze-embedded with OCT compound (Miles Inc, Naperville, Ill.). After embedding, the jaw bone was prepared into 10 μm thick sections with a cryostat (CM3050S; Leica microsystems), and immunostaining of these tissue sections was carried out.

In order to detect nerve fibers in the periodontal membrane formed around the implant, neurofilament which is a nerve fiber marker was immunostained. The primary antibody employed was neurofilament SMI312 (mouse anti-NF Ab; 1:1000, Abcam, Cambridge, Mass.), and the secondary antibody employed was Alexa Fluor594-conjugated goat anti-rat IgG (1:500, Molecular Probes). These immunostaining images were detected for fluorescence with a laser microscope (LSM510 Meta; Carl Zeiss, Jene, Germany) to observe the nerve fibers.

In an HA implant where the periodontal membrane region is not formed, no penetration of nerve fibers stained by Neurofilament (NF) was observed. On the other hand, NF-positive nerve fibers were observed in the periodontal membrane tissue of a dental follicle-attached HA implant that formed periodontium, similarly to a natural tooth (FIG. 15). From this, it was shown that the dental follicle-attached HA implant can enable formation of periodontal membrane tissue having nerve fibers after transplantation.

Example 6

Functional Analysis of Nerve Fibers in Periodontal Membrane Tissue Formed after Implant Transplantation When noxious stimulation is applied to the dental tissue by excessive occlusal force and the like, peripheral nerves oriented to the periodontal membrane project the noxious stimulation to the nucleus tractus spinalis trigemini of the medulla to thereby perceive pain. This mechanism enables avoidance/suppression of tissue injury or dysfunctionalization, and is related to biological defense. Accordingly, it is important for an implant having periodontium to not only have nerve fibers formed but to also have these peripheral nerves connectively functioning with the central nerve.

Accordingly, it was evaluated whether it was possible that nerve fibers penetrated in the periodontal membrane formed around the implant after transplantation of the dental follicle tissue-attached HA implant may transmit noxious stimulation to the central nerve. The evaluation method was performed by applying experimental orthodontic force to a natural tooth, an HA implant on Day 21 after transplantation, and a dental follicle-attached HA implant on Day 21 after transplantation, and then analyzing the expression of c-Fos protein induced for production in the nucleus tractus spinalis trigemini which is a pain stimulation indicator.

Specifically, similarly to the method of Example 2, a dental follicle-attached HA implant and an HA implant were first transplanted to a C57/BL/6 mouse. The mouse was fixed under deep anesthesia on Day 21 after transplantation. Similarly to Example 4, an orthodontic force at 10-15 g was loaded from the lingual towards the buccal against a natural first molar and an implant that survived on the jaw bone. At 2 hours after the start of orthodontic stimulation, the thoracic wall the mouse under anesthesia was opened with scissors. A 25 G needle was then inserted from the lower left ventricle where the heart was exposed, and PBS (−) solution was systemically perfused from the heart with a peristaltic pump. The left atrium was also excised to reserve blood removal route. Once blood is completely removed, 4% paraformaldehyde solution was subsequently similarly systemically refluxed for fixing.

Then, the medullary tissue was resected from inside the cranial bone of a mouse similarly to the method described in Example 5, and immersed in each of 12.5% (w/v) and 25% (w/v) sucrose solutions in order for 12 hours. After immersion, the medullary tissue was freeze-embedded with OCT compound (Miles Inc, Naperville, Ill.). After embedding, 40 μm thick sections were prepared with a cryostat (CM3050S; Leica microsystems).

The prepared sections were blocked for endogenous peroxidases by methanol supplemented with 0.3% $H_2O_2$, and blocked with 3% serum. This was then reacted with anti-c-Fos Ab (1:10,000, Santa Cruz Biotechnology, Santa Cruz, Calif.), and reacted with peroxidase-labelled goat anti-rabbit IgG (1:300, Cappel Laboratories, Aurora, Ohio) as the primary antibody. PAP immune complex (1:3000, Cappel) was then employed for immunostaining.

Expression of c-Fos protein was not observed in the orthodontic force loading to the HA implant. For the natural tooth and the dental follicle-attached HA implant, c-Fos expression was observed at 2 hours after orthodontic stimulation, thus showing that the noxious stimulation to the periodontal membrane was transmitted to the central nerve (FIG. 16). From these results, it was shown that when a dental follicle-attached HA implant was transplanted, neural function that can transmit noxious stimulation is formed in the periodontal membrane around the implant.

Example 7

Analysis of Alveolar Bone Regeneration after Implant Transplantation in Three-Wall Bone Defect Model In order to clarify whether regeneration of the alveolar bone is possible by transplantation of a dental follicle-attached HA implant, a three-wall bone defect model missing bone on one side of the alveolar bone at the implant transplantation site was prepared, a dental follicle-attached HA implant was transplanted to said model, and then the regenerated amount of the alveolar bone was analyzed.

The mandibular first molar of a 4 weeks-old C57BL/6 mouse was extracted, and 2-3 weeks of bone tissue healing period was allowed. Incision/detachment of the gingiva at the same site was then carried out, a dental micromotor (Viva-Mate Plus, NSK, Tokyo, Japan) and a dental reamer (MANI, Tochigi, Japan) were employed to cut the alveolar bone, and a transplantation fossa having a diameter of 0.8 mm and a depth of 1.2 mm was formed. The buccal bone of the alveolar bone where the transplantation fossa is present was removed with a tapered fissure-type carbide bur (MANI, Tochigi, Japan), and a three-wall bone defect model missing the buccal bone was prepared (FIG. 17). A dental follicle-attached HA implant or an HA implant was transplanted to the transplantation fossa, and the gingiva was sutured with an 8-0 nylon surgical suture (BEAR Medic, Chiba, Japan). Micro CT images of the mouse with transplantation of the implant were obtained immediately after transplantation, as well as at Day 14, Day 28, and Day 50 from transplantation with a micro CT device (In vivo Micro X-ray CT System; R_mCT, Rigaku, Tokyo, Japan). Moreover, the obtained micro CT image (slice image) data was three-dimensionally constructed with an integrated image processing software (i-VIEW-3DX, Morita, Osaka, Japan) to obtain a three-dimensional CT image. Using the micro CT images and the three-dimensional CT image obtained, the regeneration of buccal bone in the alveolar bone at the transplantation site was evaluated over time.

At this time, as a control segment, a sample in which only a three-wall bone defect was prepared without implant transplantation was prepared, and the regeneration of buccal bone in the alveolar bone was similarly evaluated over time.

Three-dimensional CT images for a segment without transplantation of an implant to a three-wall bone defect model segment, a segment with transplantation of an HA implant to a three-wall bone defect model, and a segment with transplantation of a dental follicle-attached HA implant to a three-wall bone defect model immediately after transplantation, as well as at Day 14, Day 28, and Day 50 from transplantation are shown in FIG. 18. In the segment with transplantation of an HA implant and the segment without transplantation of an implant, regeneration of the alveolar bone could be observed to some extent on Day 50, but the alveolar bone did not regenerate to the position that it should exist by nature (dotted line in the Figure). In particular, in the segment with transplantation of an HA implant, the implant itself had sunken into the alveolar bone. On the other hand, in the segment with transplantation of a dental follicle-attached HA implant, the alveolar bone had been almost completely restored on Day 50 after transplantation. Moreover, the dental follicle-attached HA implant itself had also maintained a position similar to the position at the time of transplantation in the alveolar bone to which it was transplanted to.

Micro CT images of a three-wall bone defect model with transplantation of a dental follicle-attached HA implant on Day 14, Day 28, and Day 50 from transplantation are also shown in FIG. 19. Regeneration of the alveolar bone is seen at Day 14 from transplantation, and almost completely restored alveolar bone could be observed on Day 50 from transplantation. Here, a periodontal space-like gap was observed between the regenerated alveolar bone and the dental follicle-attached implant (arrowheads in FIG. 19). As such, a dental follicle-attached implant could enable not only periodontal membrane formation but also survival of the implant accompanied by alveolar bone regeneration.

Further, for three types of segments which are a segment with transplantation of a dental follicle-attached HA implant to a three-wall defect model, a segment with transplantation of an HA implant to a three-wall defect model, and a three-wall bone defect without transplantation of an implant, a merged image of images on transplantation Day 0 and Day 50 was created, and the regenerated area of the alveolar bone was quantified. The result is shown in FIG. 20. As shown in FIG. 20, significantly high regenerated amount of the alveolar bone was observed in the dental follicle-attached HA implant transplantation segment compared to the other two segments.

Moreover, in order to evaluate the sinking of the implant after transplantation into the alveolar bone, vertical migration amount of the implant on transplantation Day 0 and Day 50 from transplantation were measured in a segment with transplantation of an HA implant to a transplantation fossa created similarly to Example 2 (not a three-wall bone defect), a segment with transplantation of an HA implant to a three-wall bone defect model, and a segment with transplantation of a dental follicle-attached HA implant to a three-wall bone defect model, and then graphed (FIG. 21 and FIG. 22). As a result, sinking of the transplanted implant was observed in the segment with transplantation of an HA implant to a three-wall bone defect model, whereas sinking of the implant was not observed in the segment without alveolar bone loss (with transplantation of an HA implant to the transplantation fossa and the segment with transplantation of a dental follicle-attached HA implant to a three-wall bone defect model. From this, it was suggested that the sinking of the implant itself is prevented by transplantation of a dental follicle-attached HA implant.

Sequence Listing

OCTP1103P1F sequence table.txt

The invention claimed is:

1. A dental implant that enables functional periodontium formation,
   comprising a physically cut tissue resected from a dental follicle placed on a surface of the dental implant,
   wherein the physically cut tissue resected from the dental follicle is a cell mass that at least partially maintains the functional binding between cells that form the tissue and retains a form that allows discrimination between the exterior and the interior of the tissue and only the interior of the tissue is placed in contact with the surface of the dental implant; and
   at the time of transplantation the dental implant retains the physically cut tissue on its surface and the surface of said implant on which said resected tissue is placed is the whole or a part of the surface which is surrounded by alveolar bone of a recipient.

2. The implant according to claim 1, wherein the dental implant is correctable after implant transplantation.

3. The implant according to claim 1, wherein said periodontium formed has at least one characteristic among:
   (i) having functional cementum and functional periodontal membrane, and
   (ii) having functional nerve fiber.

4. The implant according to claim 1, wherein said implant further comprises a coating layer of a surface coating agent on the entire surface of the implant or a part thereof, and said physically cut tissue resected from the dental follicle is placed on the surface of said coating layer.

5. The implant according to claim 4, wherein said surface coating agent is selected from the group consisting of hydroxyapatite, α-tricalcium phosphate, β-tricalcium phosphate, and collagen.

6. The dental implant of claim 1, wherein the physically cut tissue is resected in a form of strips that are placed on the dental implant surface without overlapping.

7. A method for manufacturing a dental implant that enables the formation of functional periodontium, the method comprising:
   placing a physically cut tissue resected from a dental follicle on an entire surface of a dental implant or a part thereof,
   wherein the physically cut tissue resected from the dental follicle is a cell mass that at least partially maintains the functional binding between cells that form the tissue and retains a form that allows discrimination between the exterior and the interior of the physically cut tissue such that the interior of the tissue is placed in contact with the surface of the dental implant, the implant surface or a part thereof is surrounded by alveolar bone of a recipient at the time of transplantation of said implant, and the dental implant with the physically cut tissue retains the physically cut tissue at the time of transplantation.

8. The method for manufacturing an implant according to claim 7, wherein said implant is correctable after transplantation of said implant.

9. The method for manufacturing an implant according to claim 7, wherein said periodontium formed has at least one characteristic among:
   (i) having functional cementum and functional periodontal membrane, and
   (ii) having functional nerve fiber.

10. The method for manufacturing an implant according to claim 7, wherein the method further comprises, before the step of placing said physically cut tissue resected from the dental follicle, forming a coating layer comprising a surface coating agent on the entire surface of the implant or a part thereof, and wherein said physically cut tissue is placed on the surface of said coating layer.

11. The method for manufacturing an implant according to claim 10, wherein said surface coating agent is selected from the group consisting of hydroxyapatite, α-tricalcium phosphate, β-tricalcium phosphate, and collagen.

12. The method of claim 7, wherein the physically cut tissue is resected in a form of strips that are placed on the dental implant surface without overlapping.

13. A method for transplanting a dental implant in an animal that has lost a tooth, comprising:

transplanting at a site of tooth loss a dental implant that enables functional periodontium formation, the dental implant comprising:

a physically cut tissue resected from a dental follicle placed on a surface of the dental implant, wherein the physically cut tissue resected from the dental follicle is a cell mass that at least partially maintains the functional binding between cells that form the tissue and retains a form that allows discrimination between the exterior and the interior of the tissue such that the interior of the tissue is placed in contact with the surface of the dental implant;

the surface of said implant on which said resected tissue is placed is the whole or a part of the surface which is surrounded by alveolar bone of a recipient at the time of transplantation of said implant; and the dental implant is transplanted with the physically cut tissue on its surface.

14. The method for transplanting an implant according to claim 13, wherein said animal is a non-human mammal.

15. The method for transplanting an implant according to claim 13, wherein said animal is a human.

16. The method of claim 13, wherein the physically cut tissue is resected in a form of strips that are placed on the dental implant surface without overlapping.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: mouse osteocalcin forward primer

<400> SEQUENCE: 1
tagcagacac catgaggacc                    20

```
<210> SEQ ID NO 2
<211> LENGTH: 20
<212> TYPE: DNA
<213> ORGANISM: Artificial
<220> FEATURE:
<223> OTHER INFORMATION: mouse osteocalcin reverse primer

<400> SEQUENCE: 2
tgacatccat acttgcaggg                                            20

<210> SEQ ID NO 3
<211> LENGTH: 20
<212> TYPE: DNA
<213> ORGANISM: Artificial
<220> FEATURE:
<223> OTHER INFORMATION: mouse colony stimulating factor 1 forward
      primer

<400> SEQUENCE: 3
tactgaacct gcctgctgaa                                            20

<210> SEQ ID NO 4
<211> LENGTH: 20
<212> TYPE: DNA
<213> ORGANISM: Artificial
<220> FEATURE:
<223> OTHER INFORMATION: mouse colony stimulating factor 1 reverse
      primer

<400> SEQUENCE: 4
ccagagcttg tgacaggaca                                            20
```